(12) United States Patent
Yue et al.

(10) Patent No.: US 8,192,466 B2
(45) Date of Patent: Jun. 5, 2012

(54) CONICAL INTERSPINOUS APPARATUS AND A METHOD OF PERFORMING INTERSPINOUS DISTRACTION

(75) Inventors: James J. Yue, Guilford, CT (US); Jared Arambula, San Diego, CA (US); Christian Gabriel Gamboa, San Diego, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 245 days.

(21) Appl. No.: 12/616,245

(22) Filed: Nov. 11, 2009

(65) Prior Publication Data

US 2010/0106191 A1  Apr. 29, 2010

Related U.S. Application Data

(63) Continuation-in-part of application No. 12/343,082, filed on Dec. 23, 2008.

(60) Provisional application No. 61/092,142, filed on Aug. 27, 2008.

(51) Int. Cl.
*A61B 17/70* (2006.01)

(52) U.S. Cl. ......................................... 606/249; 606/279
(58) Field of Classification Search .................. 606/246, 606/248, 249, 279, 90, 104; 623/17.11–17.16
See application file for complete search history.

(56) References Cited

U.S. PATENT DOCUMENTS

2010/0234889 A1* 9/2010 Hess ............................ 606/249
* cited by examiner

*Primary Examiner* — Eduardo C Robert
*Assistant Examiner* — Christina Negrelli
(74) *Attorney, Agent, or Firm* — Michael R. Shevlin

(57) ABSTRACT

A conical interspinous apparatus comprising: an insertion portion with a proximal end, a distal end, and conical screw-shaped grooves configured to distract two adjacent spinous processes; a shaft portion, coupled to the distal end of the insertion portion, and having a smaller cross-section than a cross-section at the distal end of the insertion portion, such that the two spinous processes rest on the shaft portion; and a clamp portion being movable and securable along the shaft, and being configured to secure the two spinous processes between the clamp portion and the distal end of the insertion portion.

16 Claims, 22 Drawing Sheets

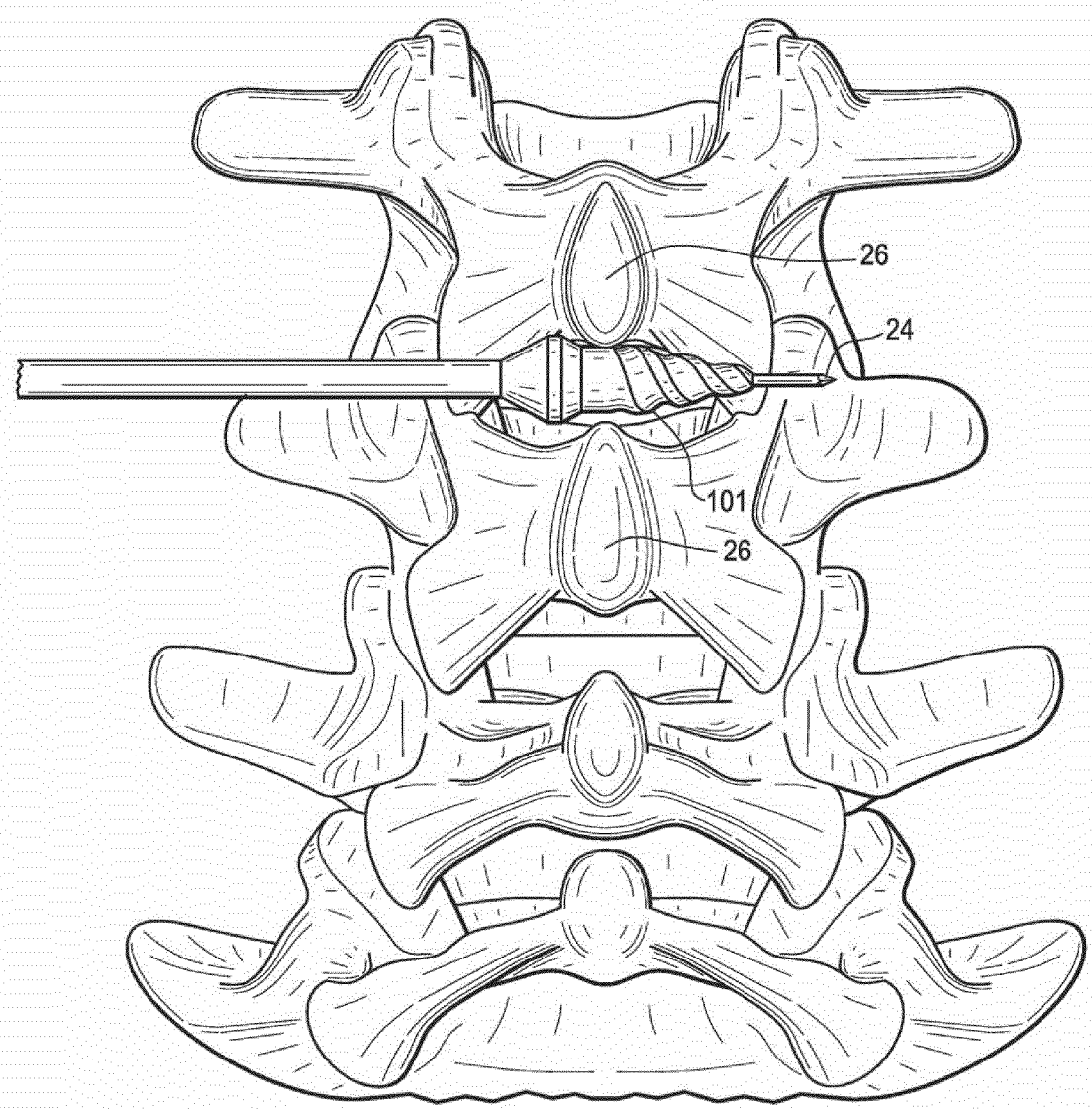

CONICAL INTERSPINOUS APPARATUS AND A METHOD OF PERFORMING INTERSPINOUS DISTRACTION

CROSS-REFERENCE TO RELATED APPLICATION

The present application is a continuation-in-part of U.S. patent application Ser. No. 12/343,082, filed on Dec. 23, 2008, which claims priority from U.S. Provisional Application No. 61/092,141, filed on Aug. 27, 2008, both of which are incorporated herein by reference in their entirety.

BACKGROUND OF THE INVENTION

1. Field of the Invention

The present invention relates to the field of interspinous devices, and more particularly, relates to conical interspinous apparatus inserted between two spinous processes of the lumbar spine such that the two spinous processes are separated, the spinal canal opens and the symptoms of spinal stenosis are alleviated. Thus, the conical interspinous apparatus can be used to treat spinal stenosis.

2. Description of the Related Art

Lumbar Spinal Stenosis (LSS) is one of the most common reasons for spine surgery in older people. Spinal stenosis is a medical condition in which the spinal canal narrows and compresses the spinal cord and nerves. This is usually due to the natural process of spinal degeneration that occurs with aging. It can also sometimes be caused by spinal disc herniation, osteoporosis or a tumor. Spinal stenosis may affect the cervical or lumbar vertebrae or both. Lumbar spinal stenosis results in lower back pain as well as pain or abnormal sensations in the legs, thighs, feet or buttocks, or loss of bladder and bowel control.

Laminectomy is a basic part of the surgical treatment of LSS and is the most effective remedy for severe spinal stenosis Laminectomy can be done without spinal fusion. However, if the spinal column is unstable, fusion may be required for the laminectomy.

Therefore, a device which can be implanted between two spinous processes of the spine more easily and which involves less invasive procedures than present day procedures is needed. Also, a device which can easily be adapted for both fusion and non-fusion procedures is needed. Such a device would aid in the treatment for spinal stenosis.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above. The present invention provides conical interspinous apparatus inserted between two spinous processes of the lumbar spine such that the two spinous processes are separated, and a method of performing interspinous distraction.

According to an exemplary embodiment of the present invention, provided is a conical interspinous apparatus including an insertion portion with a proximal end, a distal end, and conical screw-shaped grooves configured to distract two adjacent spinous processes; a shaft portion, coupled to the distal end of the insertion portion, and having a smaller cross-section than a cross-section at the distal end of the insertion portion, such that the two spinous processes rest on the shaft portion; and a clamp portion being movable and securable along the shaft, and being configured to secure the two spinous processes between the clamp portion and the distal end of the insertion portion.

Another exemplary embodiment of the present invention is a method of performing interspinous distraction, the method comprising: inserting a distractor having a conical insertion portion and a shaft between two spinous processes of vertebrae, the conical insertion portion configured such that a gradual distraction between the two spinous processes occurs; inserting an insertion driver while coupled to the distractor, the insertion driver being detachably coupled to a rear portion of the distractor; implanting the distractor between the two spinous processes such that the two spinous processes rest on the shaft between a proximal end and a distal end of the shaft; advancing a clamp along the shaft until it abuts the spinous process; tightening the clamp; and decoupling the insertion driver from the distractor and removing the insertion driver.

Thus, a device which can be implanted between two spinous processes of the spine more easily and which involves less invasive procedures is provided which can be adapted for both fusion and non-fusion procedures.

BRIEF DESCRIPTION OF THE DRAWINGS

The above and other aspects of the present invention will become more apparent from the following description of exemplary embodiments, taken in conjunction with the accompanying drawings of which:

FIGS. 13A-13I illustrate a method of performing interspinous distraction according to an exemplary embodiment of the present invention.

Throughout the drawings, the same drawing reference numerals will be understood to refer to the same elements, features, and structures.

DETAILED DESCRIPTION OF THE EXEMPLARY EMBODIMENTS

The matters defined in the description such as a detailed construction and elements are provided to assist in a comprehensive understanding of the embodiment of the invention and are merely exemplary. Accordingly, those of ordinary skill in the art will recognize that various changes and modifications of the embodiment described herein can be made without departing from the scope and spirit of the invention. Also, descriptions of well-known functions and constructions are omitted for clarity and conciseness.

The device is composed of a device which has a pointed conical shape with embedded screw-shaped (i.e., helical) grooves that permit the passage of the device between the spinous processes of the human spine. The device is designed to be positioned between two spinous processes. It is placed through the interspinous ligament and below the supra-spinous ligament. The grooved conical surface permits the device to be screwed into place in a percutaneous or traditional open surgery. The device is secured between the spinous processes due to a deeper central engagement groove as well as by mechanisms to be described whereby the end(s) of the device are further stabilized. Due to its position within the interspinous ligament and below the supra-spinous ligament, further stability is obtained.

Furthermore, due to its geometric shape, the device gradually spreads the spinous processes apart. By spreading the spinous processes apart, the volume of the spinal canal and vertebral foramen are increased thereby decompressing the spine in cases of spinal stenosis.

A unique feature of this procedure is that there is no required instrumentation to place the final device into its final position except for a device holding tool (i.e., an insertion driver). Provisional dilation of the spinous processes can be performed if so desired with solid dilators also of conical screw or a smooth semi-conical shape. The depth and pitch and other parameters of a screw configuration can be modified to provide faster insertion, more stable insertion, and positioning of the implant. The central groove may be of a smaller cross-section than the insertion portion and broader to accept the spinous process anatomic region in a stable and consistent manner. The device can be either solid or cannulated.

Figure 1:
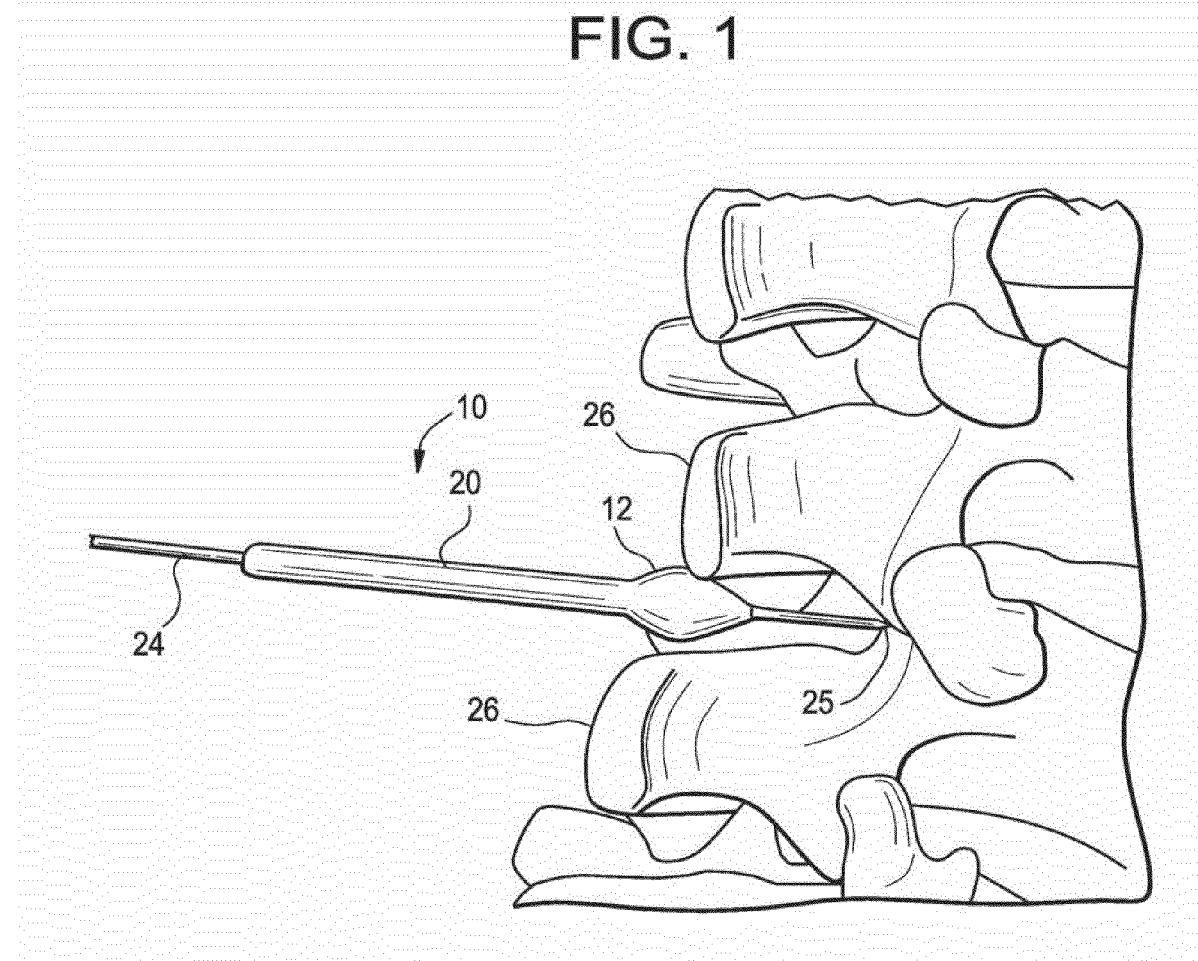
FIG. 1 illustrates an interspinous apparatus according to an exemplary embodiment of the present invention.

FIG. 1 illustrates a high level drawing of an interspinous apparatus 10 according to an exemplary embodiment of the present invention. The interspinous apparatus 10 includes a distractor 12, an insertion driver 20, and a guide wire 24 having a pointed tip 25. The distractor 12 has a conical shape which is configured to enable passage of the distractor 12 between two spinous processes 26 of vertebrae such that a gradual distraction between the two spinous processes 26 occurs. Each of the distractor 12 and the insertion driver 20 have a guide channel which extends through an entire central portion therein configured to accept the guide wire 24 therein. The pointed tip 25 of the guide wire 24 permits an easier insertion of the guide wire 24 between the two spinous processes 26. The guide wire 24 is inserted between the two spinous processes 26 in order to guide the insertion of the distractor 12, detachably coupled to the insertion driver 20, between the two spinous processes 26.

The distractor 12 has a conical shape which is adapted to enable passage of the distractor 12 between two spinous processes 26 that a gradual distraction between the two spinous processes 26 occurs. Due to the conical shape of the distractor 12, the distractor 12 has an axis of distraction, to be described later, having a constant increasing angle that provides for constant distraction.

The distractor 12 can be composed of any solid or semi solid material including but not limited to poly-ether-ether-ketone (PEEK), titanium, stainless steel, or bone. In addition, the distractor 12 may be composed of but not limited to hydroxyapatite, bone substitutes, a combination of hydroxyapatite and bone cement, CORTOSS, or the like. If the distractor 12 is composed of any material besides bone, motion is preserved due to the rolling effect of the cone in extension and flexion. If the distractor 12 is composed of bone, the device can be used to induce fusion. Thus, the device could also be used to fuse spines depending on what material it is made of.

If less motion is so desired, the central engagement groove 14 can be partially flattened thereby decreasing the rolling effect of the device providing more stability.

If the distractor 12 is composed of bone, the distractor 12 may be used to treat patients who require fusion with or without decompression of the spinal canal and foramen. In patients who do not require a fusion, materials such as PEEK, steel, titanium, or other alloys could be utilized.

Figure 2A:
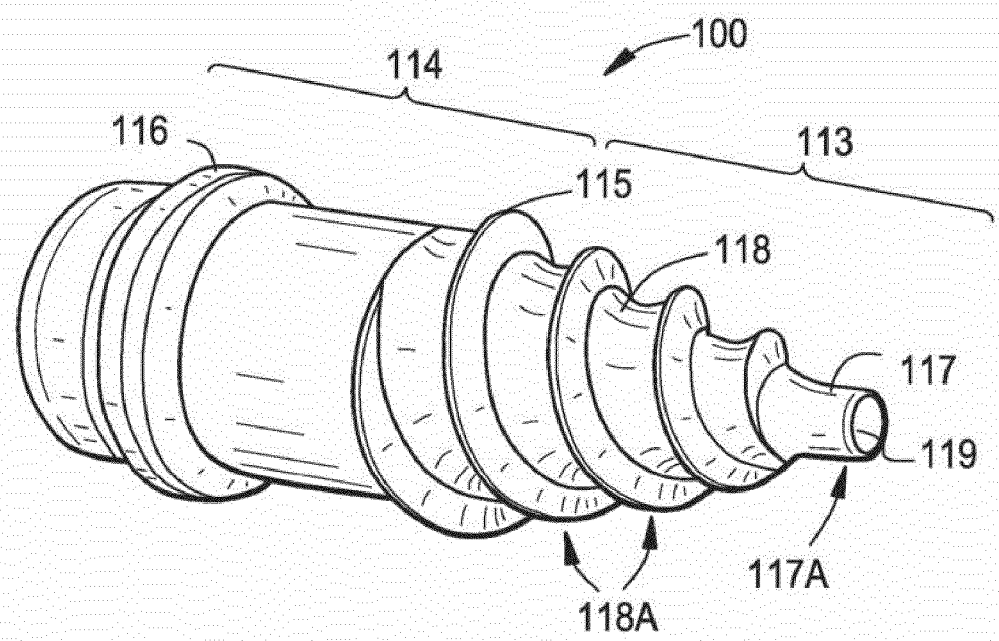
FIG. 2A illustrates a dilator according to an exemplary embodiment of the present invention.
Figure 2B:
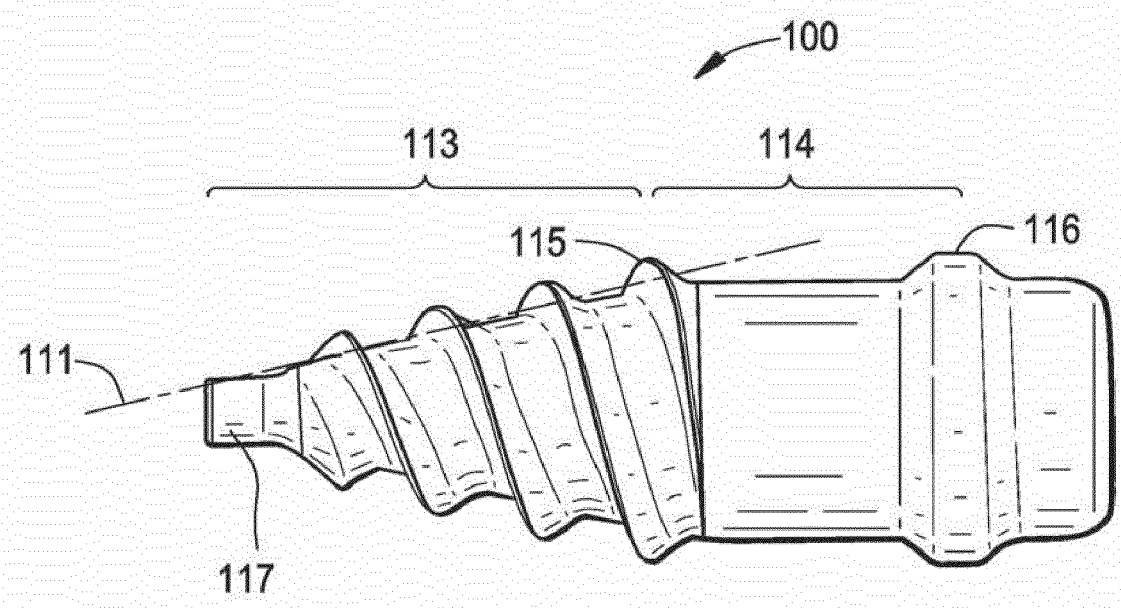
FIG. 2B illustrates another view of the dilator shown in FIG. 2A.

FIGS. 2A and 2B illustrate a solid dilator 100 that is used before the distractor 12 according to an exemplary embodiment of the present invention. The dilator 100 includes an insertion portion 113 and a central engagement groove 114 having a proximal end 115 and a distal end 116.

The insertion portion 113 has a conical shape which tapers from the proximal end 115 of the central engagement groove 114 to a tip 117 and is adapted to enable passage of the dilator 100 between the two spinous processes 26 such that a gradual distraction between the two spinous processes 26 occurs. The insertion portion 113 has embedded screw-shaped (i.e., helical) grooves 118 which permits the device to be screwed into place in a percutaneous or traditional open surgery. The grooves 118 include sharp edges 118A that are configured to incise through a patient's interspinous ligament (not shown). Because the sharp edges 118A are also screw-shaped (i.e., helical), the edges 118A can serially dilates/spread the interspinous ligament apart. Moreover, the concave grooves 118 dilator keep the interspinous ligament distracted while the next edge 118A incises the ligament. The insertion portion 113 an axis of distraction 111 having a constant increasing angle that provides for constant distraction. The tip 117 of the insertion portion 113 is ungrooved to allow for ease of initial insertions, but may be grooved. Furthermore, the tip 119 is hollow, showing a portion of the guide channel 119 which extends through the entire central portion of the distractor 112 for accepting the guide wire 124 therein. The tip 119 also includes a sharp edge 119A this is configured to cut through the patient's interspinous ligament.

The central engagement groove 114 is adapted to secure the dilator 100 between the two spinous processes 26 such that the two spinous processes 26 rest in the central engagement groove 14 between the proximal end 115 and the distal end 116.

Figure 3:
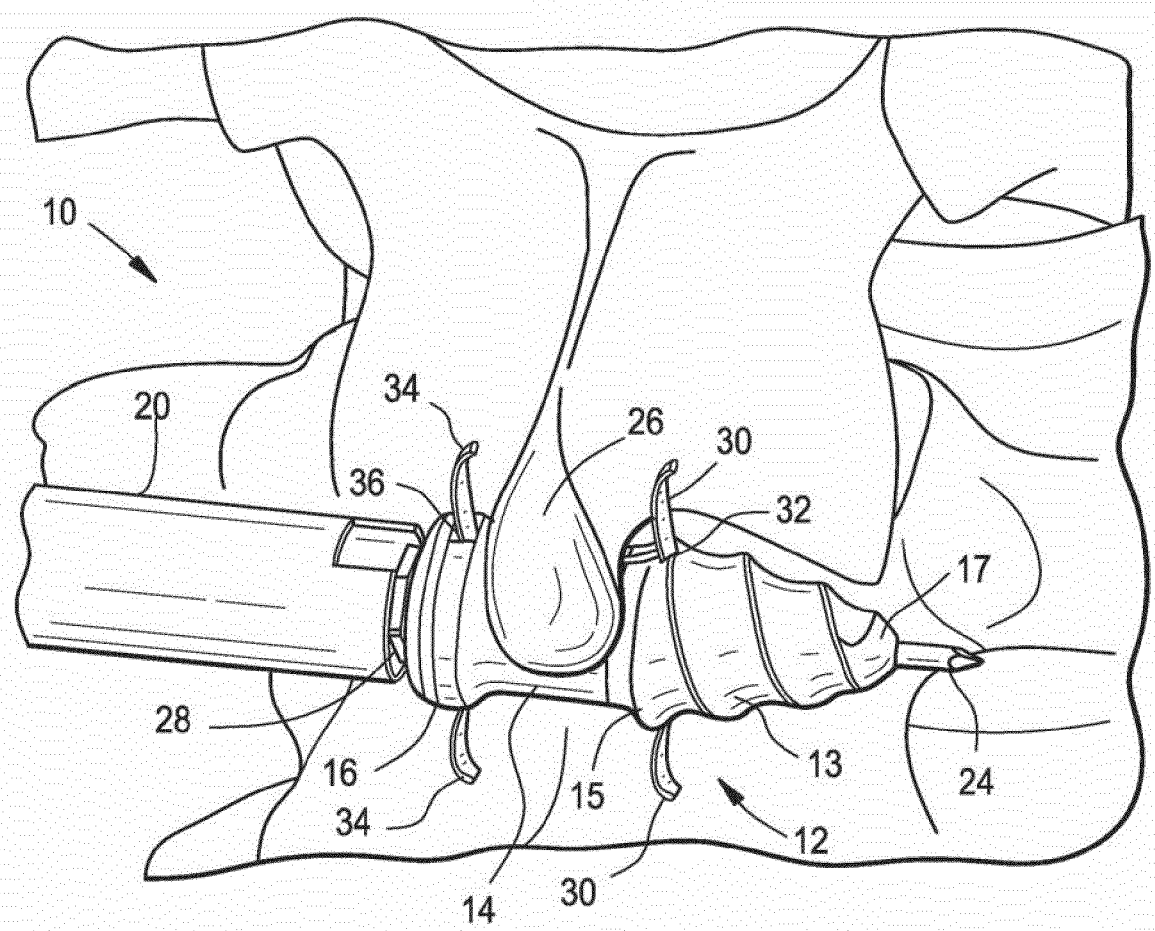
FIG. 3 illustrates an interspinous apparatus according to an exemplary embodiment of the present invention.

FIG. 3 illustrates an interspinous apparatus 10 according to another exemplary embodiment of the present invention. The distractor is inserted after the dilator 100 is removed and includes an insertion portion 13 and a central engagement groove 14 having a proximal end 15 and a distal end 16.

Like the dilator 100, the insertion portion 13 has a conical shape which tapers from the proximal end 15 of the central engagement groove 14 to a tip 17 and is adapted to enable passage of the distractor 12 between the two spinous processes 26 such that a gradual distraction between the two spinous processes 26 occurs. The insertion portion 13 has embedded screw-shaped (i.e., helical) grooves 18 which permits the device to be screwed into place in a percutaneous or traditional open surgery. The insertion portion 13 an axis of distraction 11 having a constant increasing angle that provides for constant distraction. The tip 17 of the insertion portion 13 is ungrooved to allow for ease of initial insertions, but may be grooved. Furthermore, the tip 19 is hollow, showing a portion of the guide channel 19 which extends through the entire central portion of the distractor 12 for accepting the guide wire 24 therein.

The central engagement groove 14 is adapted to secure the distractor 12 between the two spinous processes 26 such that the two spinous processes 26 rest in the central engagement groove 14 between the proximal end 15 and the distal end 16.

The interspinous apparatus 10 includes the distractor 12 having a rear portion 28 detachably coupled to the insertion driver 20, and the guide wire 24. The insertion portion 13, as shown, has a tip 17 which is grooved. In contrast to the dilator 100, the distractor 12 includes a pair of proximal stabilization wings 30 retracted within a first cavity (not shown) of the distractor 12 and configured to be deployed through a pair of proximal slots 32 disposed on opposite sides of the proximal end 15 of the central engagement groove 14. The stabilization wings 30 are deployed after the spinous processes 26 are secured in the central engagement groove 14 to inhibit the distractor 12 from reversing out from between the two spinous processes 26.

The distractor may also include a pair of distal stabilization wings 34 retracted within a second cavity (not shown) of the distractor 12 and configured to be deployed through a pair of distal slots 36 disposed on opposite sides of the distal end 16 of the central engagement groove 14. The stabilization wings 34 are deployed after the spinous processes 26 are secured in the central engagement groove 14 to inhibit the distractor from being inserted further between the two spinous processes 26. Thus, the proximal stabilization wings 30 and the distal stabilization wings 34 stabilize the two spinous processes 26 within the central engagement groove 14 and in some embodiments can additionally clamp onto the spinous processes.

Figure 4:
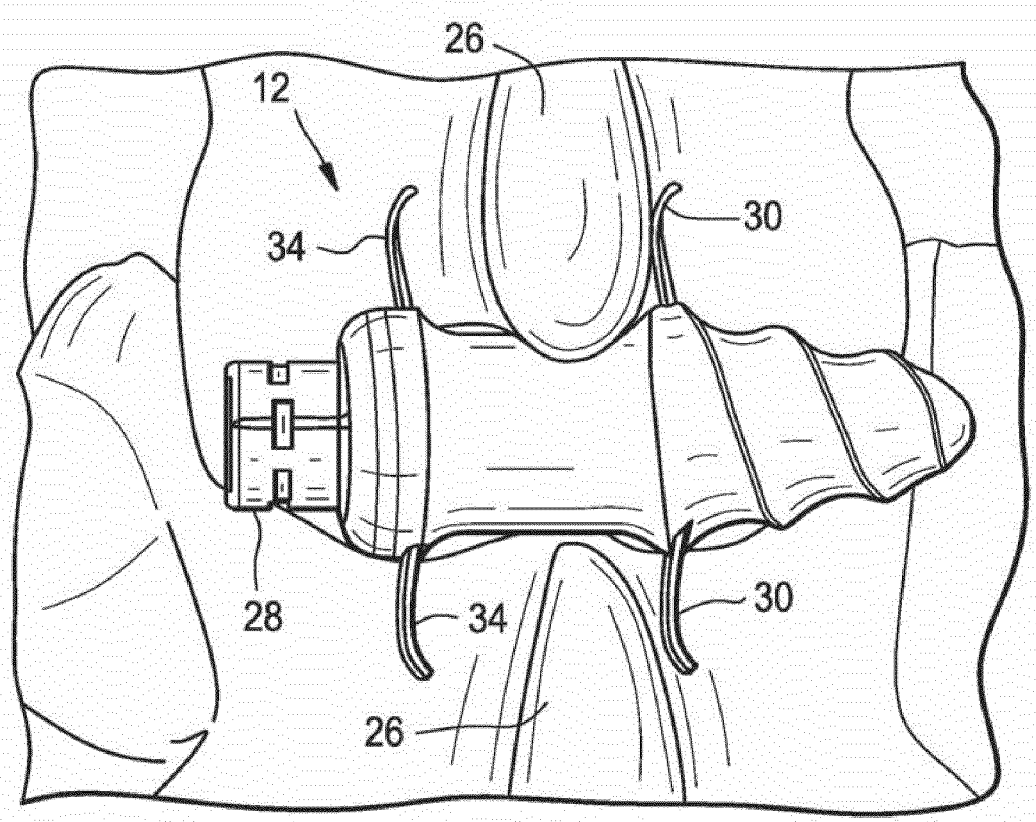
FIG. 4 illustrates an interspinous apparatus according to the exemplary embodiment of the present invention.

FIG. 4 illustrates an interspinous apparatus 10 having the insertion driver 20 decoupled from the rear portion 28 of the distractor 12 and the guide wire 24 removed from the distractor 12. Thus, the distractor 12 is shown implanted between the two spinous processes 26 and having the proximal stabilization wings 30 and the distal stabilization wings 34 deployed from within the distractor 12.

In addition, a circular ring can be slipped over either end of the device and tightened thereby providing stability to the implant (not shown).

Figure 5:
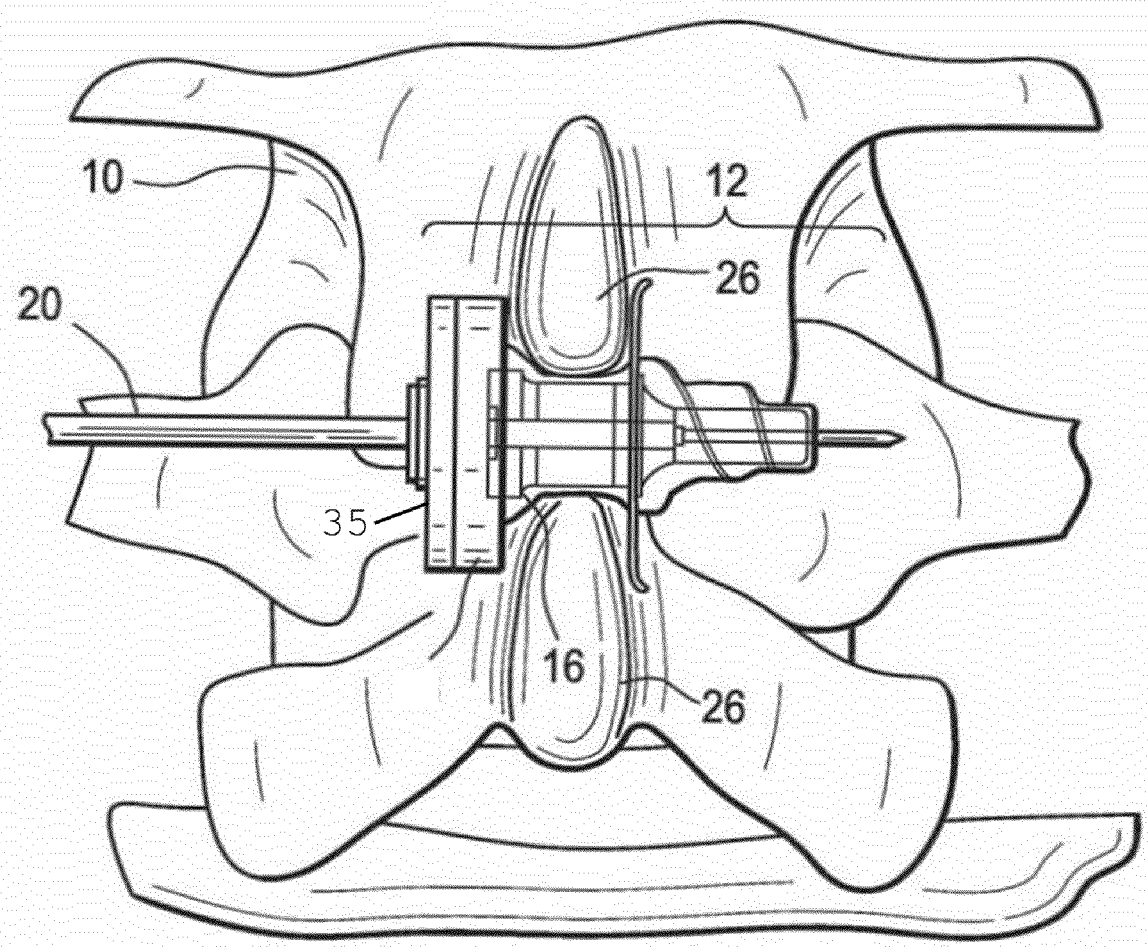
FIG. 5 illustrates an interspinous apparatus according to another exemplary embodiment of the present invention.

FIG. 5 illustrates an interspinous apparatus 10 according to another exemplary embodiment of the present invention. In particular, the distractor 12 includes a stabilization base 35 in the alternative to the distal stabilization wings 34. The stabilization base 35 is coupled to the distal end 16 of the central engagement groove 14 and which extends outward from the distractor 12. The stabilization base 35, much like the distal stabilization wings 34, is adapted to inhibit the distractor from being inserted further between the two spinous processes 26.

Figure 6A:
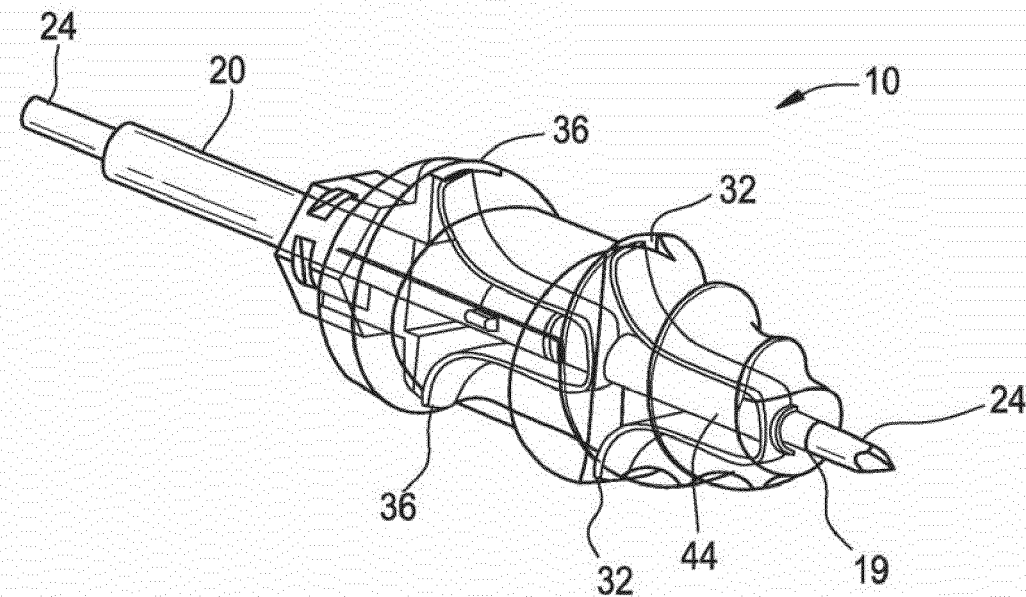
FIG. 6A illustrates an interspinous apparatus having stabilizers in a retracted state according to another exemplary embodiment of the present invention.
Figure 6B:
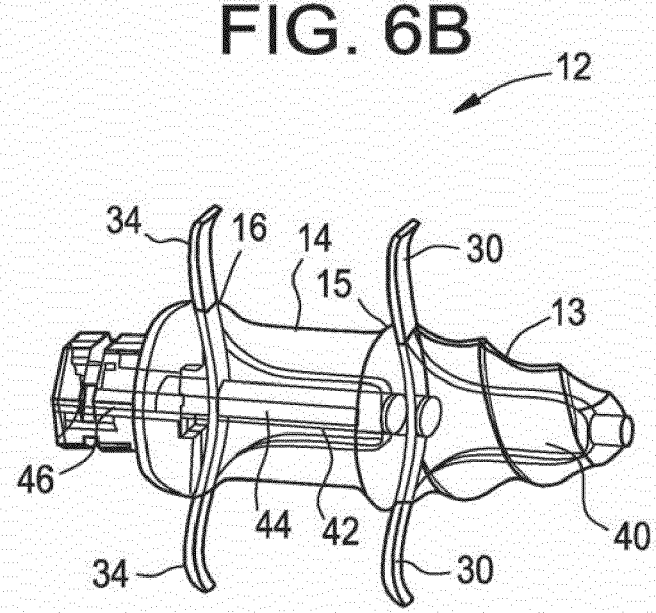
FIG. 6B illustrates an interspinous apparatus having stabilizers in a deployed state according to the exemplary embodiment of the present invention shown in FIG. 6A.

FIGS. 6A and 6B illustrate an interspinous apparatus having stabilizers 30 and 34 in a retracted state and in a deployed state, respectively, according to another exemplary embodiment of the present invention.

The guide wire 24 is disposed within the guide channel 19, which extends through the entire central portion of the distractor 12 and the insertion driver 20. Each guide channel 19 of the distractor 12 and the insertion driver 20 is in alignment with each other.

The distractor 12 includes the pair of proximal stabilization wings 30 retracted within a first cavity 40 of the distractor 12. The proximal stabilization wings 30 are configured to be deployed through the pair of proximal slots 32 disposed on opposite sides of the proximal end 15 of the central engagement groove 14. In addition, the distractor 12 includes the pair of distal stabilization wings 34 retracted within a second cavity 42 of the distractor. The distal stabilization wings 34 are configured to be deployed through the pair of distal slots 36 disposed on opposite sides of the distal end 16 of the central engagement groove 14.

The distractor 12 includes a deployment bar 44 disposed therein and detachably coupled to the insertion driver 20. The deployment bar 44 is also coupled to each stabilization wing of the proximal stabilization wings 30 and the distal stabilization wings 34. The deployment bar 44 is disposed within the guide channel 19 of the distractor 12 and is configured to be slidably switched between an extended position (as shown in FIG. 6A) and a retracted position (as shown in FIG. 6B).

Thus, when the deployment bar 44 is in the extended position, the deployment bar 44 maintains the proximal stabilization wings 30 and the distal stabilization wings 34 in a retracted state. On the other hand, when deployment bar 44 is in the retracted position, the deployment bar 44 releases the proximal stabilization wings 30 and the distal stabilization wings 34 to a deployed state. The deployment bar 44 is slidably switched between the extended position and the retracted position by moving the portion of the insertion driver 20 that is detachably coupled to the deployment bar 44 in and out of the distractor 12.

When the deployment bar 44 is an a retracted position and the stabilization wings 30 and 34 are in the deployed state, the stabilization wings 30 and 34 may be locked into their deployed position by a lock configured to engage with the deployment bar 44. For example, the portion of the insertion driver 20 that is detachably coupled to the deployment bar 44 may be rotated, and in turn rotating the deployment bar 44 within the distractor 12 to a locked position. Once in a locked state, the insertion driver 20 can be decoupled from the deployment bar 44 and removed from the guide wire 24.

Figure 7:
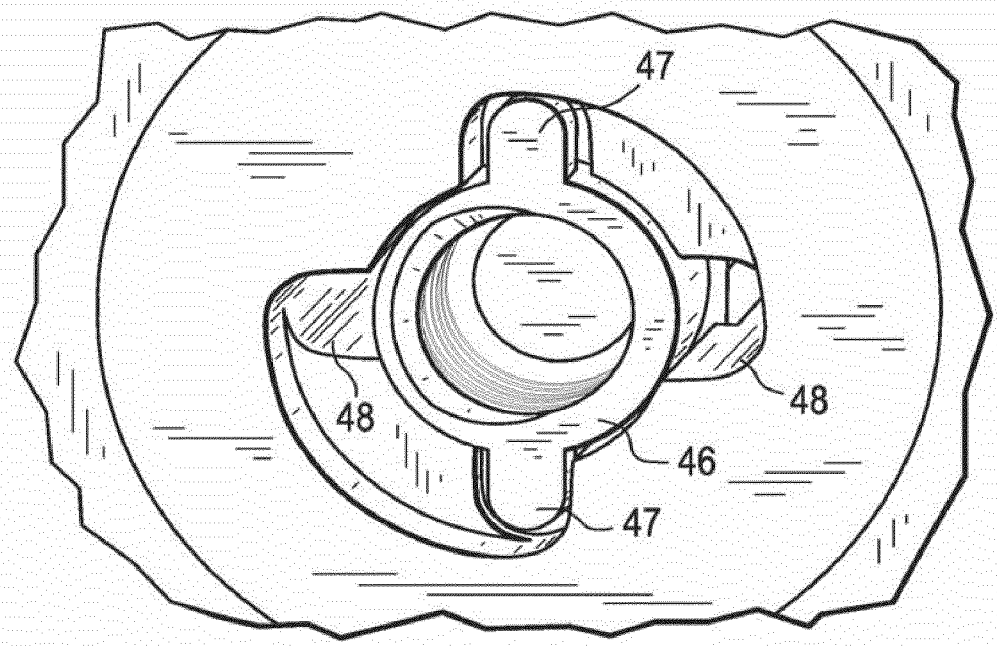
FIG. 7 illustrates a locking mechanism according to an exemplary embodiment of the present invention.

FIG. 7 illustrates a locking mechanism according to an exemplary embodiment of the present invention. In particular, a rear portion 46 (as shown in FIGS. 6A and 6B) of the deployment bar 44 has interlocking members 47 which can be rotated clockwise to engage locking slots 48 to lock the deployment bar 44 into place, and thereby, locking the stabilization wings 30 and 34 in the deployed state.

Figure 8:
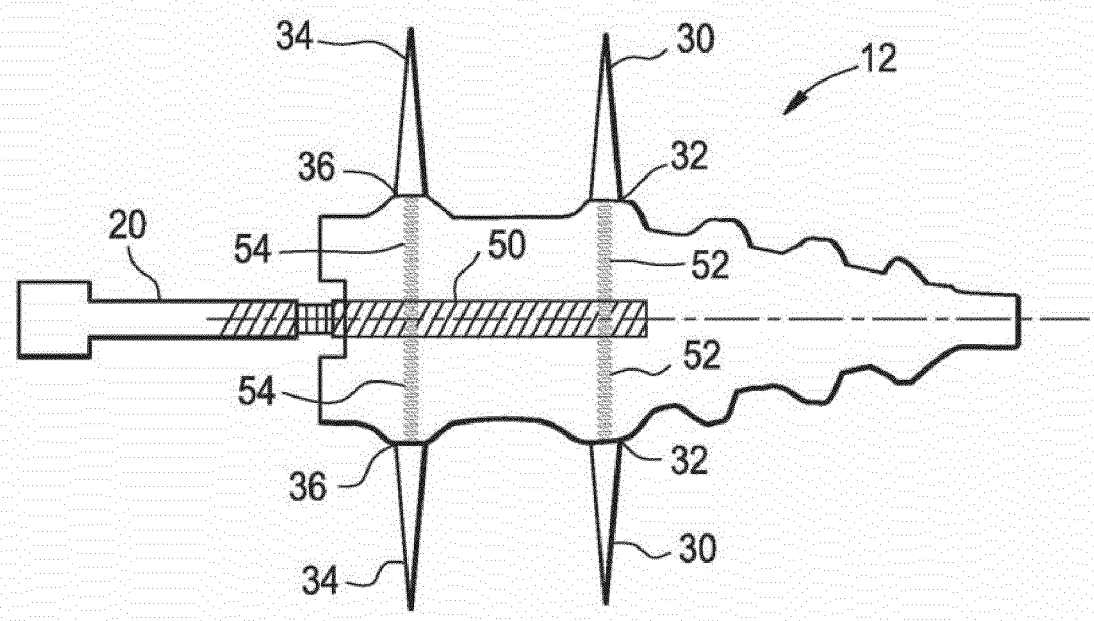
FIG. 8 illustrates an interspinous apparatus according to another exemplary embodiment of the present invention.

FIG. 8 illustrates an interspinous apparatus according to another exemplary embodiment of the present invention. In particular, FIG. 8 illustrates an alternative mechanism for deploying the proximal stabilization wings 30 and the distal stabilization wings 34. The distractor 12 includes an insertion screw driver 50 disposed within the guide channel of the distractor, coupled to the insertion driver 20 and configured to engage a first pair of gears 52 and a second pair of gears 54. Each gear 52 and 54 is mechanically coupled to a respective stabilization wing 30 and 34. Thus, when the insertion driver 20 is turned, the insertion screw driver 50 is turned within the distractor 12 and engages with the first pair of gears 52 to deploy the pair of proximal stabilization wings 30 from the proximal slots 32 and engages with the second pair of gears 54 to deploy the pair of distal stabilization wings 34 from the distal slots 36.

Figure 9:
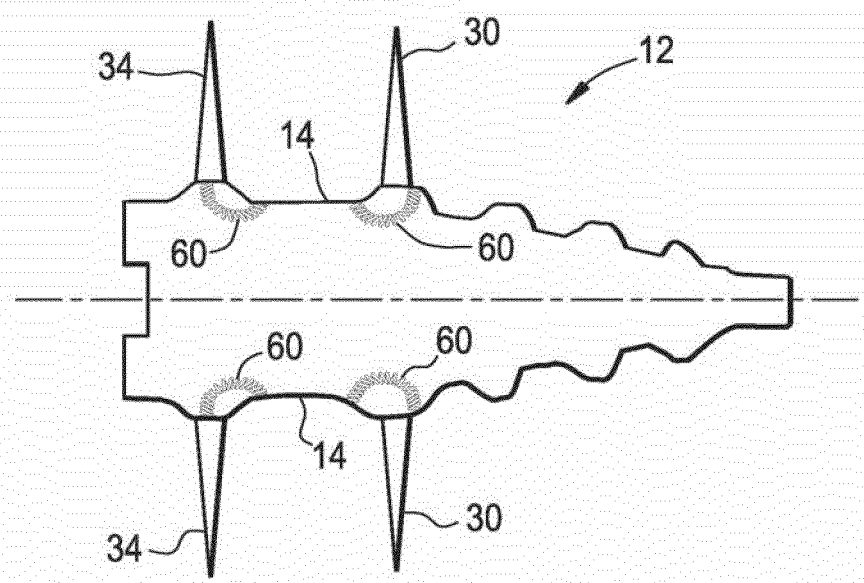
FIG. 9 illustrates an interspinous apparatus according to another exemplary embodiment of the present invention.

FIG. 9 illustrates an interspinous apparatus according to another exemplary embodiment of the present invention. In particular, FIG. 9 illustrates an alternative mechanism for deploying the proximal stabilization wings 30 and the distal stabilization wings 34.

Each stabilization wing of the pair of proximal stabilization wings 30 and the pair of distal stabilization wings 34 are coupled to the central engagement groove 14 by a pressure mechanism 60 such that the stabilization wings 30 and 34 are deployed when the central engagement groove 14 is pressurized by compression from the two spinous processes 26 upon insertion therebetween. The pressure on the central engagement groove 14 deploys the stabilization wings 30 and 34 from within the distractor 12.

Figure 10:
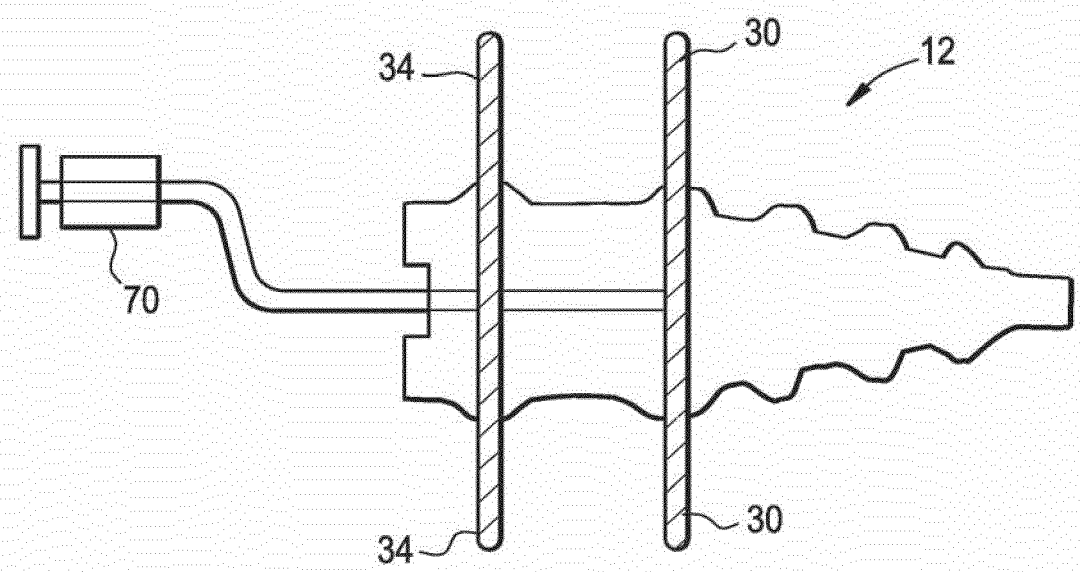
FIG. 10 illustrates an interspinous apparatus according to another exemplary embodiment of the present invention.

FIG. 10 illustrates an interspinous apparatus according to another exemplary embodiment of the present invention. In particular, FIG. 10 illustrates an alternative mechanism for deploying the proximal stabilization wings 30 and the distal stabilization wings 34.

The proximal stabilization wings 30 and distal stabilization wings are balloon O-rings such that the stabilization wings 30 and 34 are deflated in a retracted state and inflated in a deployed state.

A pump 70 coupled to each of the proximal stabilization wings 30 and distal stabilization wings 34 is used to inflate the proximal stabilization wings 30 and the distal stabilization wings to a deployed state 34. The O-rings can be inflated with either a gas or a liquid to stabilize the implant.

Figure 11A:
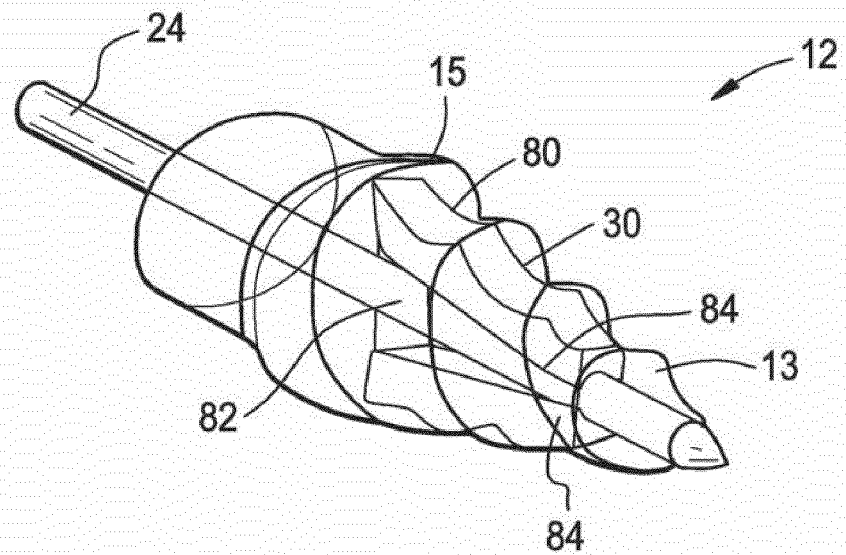
FIGS. 11A and 11B illustrate an interspinous apparatus according to another exemplary embodiment of the present invention.
Figure 11B:
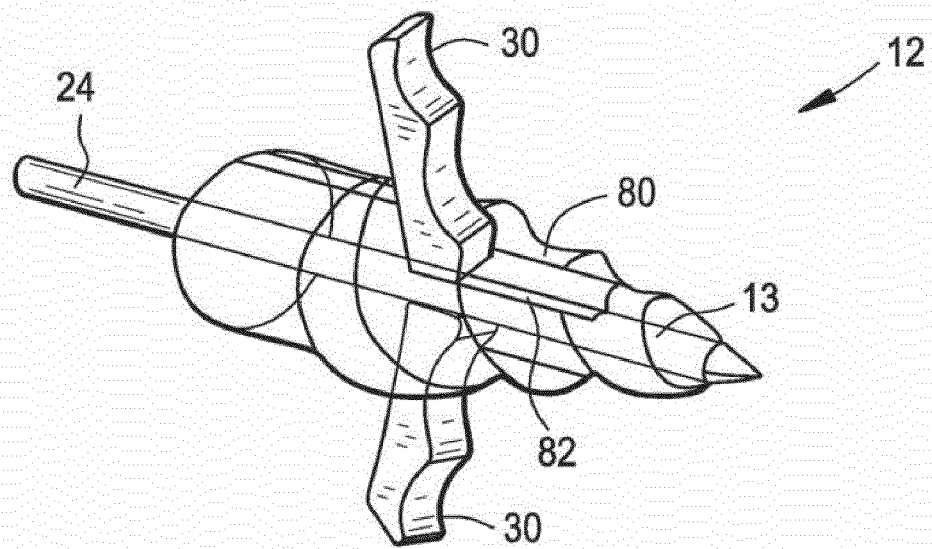

FIGS. 11A and 11B illustrate an interspinous apparatus according to another exemplary embodiment of the present invention. In particular, FIGS. 11A and 11B illustrate an alternative mechanism for deploying the proximal stabilization wings 30. FIGS. 11A and 11B illustrate an interspinous apparatus having stabilizers 30 in a retracted state and in a deployed state, respectively, according to another exemplary embodiment of the present invention.

The insertion portion 13 includes a pair of axial rectangular grooves 80, each disposed oppositely from each other. Within the pair of axial rectangular grooves 80 is disposed the pair of proximal stabilization wings 30 or side wings. Each proximal stabilization wing 30 is disposed within one of the pair of axial rectangular grooves 80. Furthermore, the proximal stabilization wings 30 are configured to be congruent with a shape of the axial rectangular grooves 80 and with a surface of the insertion portion 13 in an undeployed state as shown in FIG. 11A. Thus, if the insertion portion 13 has a conical screw shape such that the surface of the insertion portion has screw-shaped grooves 18, a surfaces of the proximal stabilization wings 30 also have grooves to be congruent the grooved surface of the insertion portion 13. This enables the distractor 12 to be screwed into place between the two spinous processes 26 when the proximal stabilization wings 30 are undeployed.

The proximal stabilization wings 30 are also configured to be deployed outward from the axial rectangular grooves 80 as shown in FIG. 11B. A deployment means 82 deploys the pair of proximal stabilization wings 30 from the axial rectangular grooves 80 by pulling the stabilization wings 30 towards the proximal end 15 of the central engagement groove 14 such that such that the stabilization wings 30 open up from the axial rectangular grooves 80 to a vertical position adjacent to the proximal end 15 of the central engagement groove 14. The stabilization wings 30 are coupled to the deployment means 82 by a pair of hinges 84, enabling the stabilization wings 30 to open to a deployed state.

The distractor 12 may also include the stabilization base 35 similar to that shown in FIG. 5.

Figure 12A:
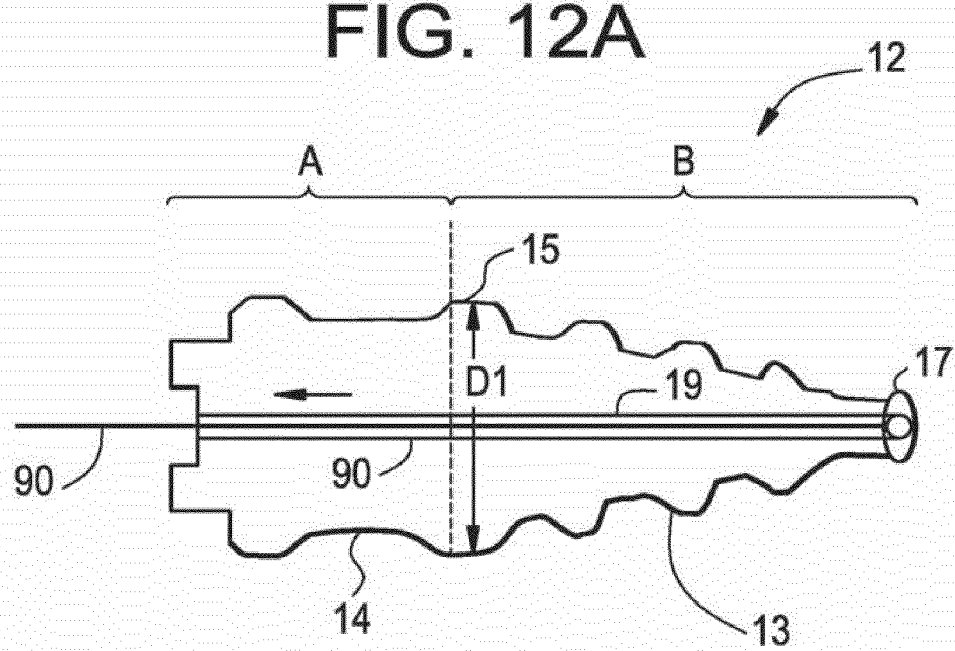
FIGS. 12A and 12B illustrate an interspinous apparatus according to another exemplary embodiment of the present invention.
Figure 12B:
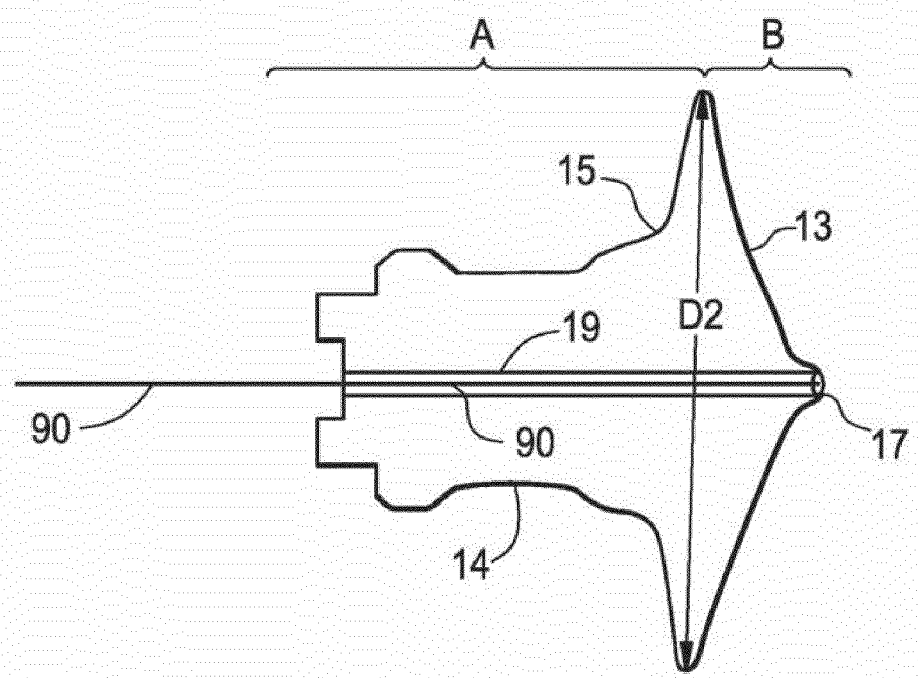

FIGS. 12A and 12B illustrate an interspinous apparatus according to another exemplary embodiment of the present invention. In particular, FIGS. 12A and 12B illustrate an alternative mechanism for deploying a stabilizer.

The distractor 12, and more particularly, the insertion portion 13 may be composed of differing materials to permit for a collapsing umbrella stabilizing tip to be deployed. The insertion portion 13 is made of flexible material having a first diameter D1 at the proximal end 15 of the central engagement groove 14. The insertion portion 13 is configured to collapse towards the proximal end of the central engagement groove such that the insertion portion 13 is compressed into a shape having a second diameter D2 at the proximal end 15 of the central engagement groove 14 larger than the first diameter D1 after the distractor 12 is implanted to inhibit the distractor 12 from reversing out from between the two spinous processes 26.

The distractor 12 includes a wire 90 fed through the guide channel 19 and connected to the tip 17 of the insertion portion 13. The tip 17 of the insertion portion 13 is adapted to be pulled towards the central engagement groove 14 upon pulling of the wire 90 to collapse the insertion portion 13. Thus, the length of portion B collapses, while the length of portion A remains constant and rigid.

The distractor 12 may also include the stabilization base 35 similar to that shown in FIG. 5.

Further, it would be understood that the stabilization base 35 as described in FIG. 5 could be implemented in any of the above exemplary embodiments.

Figure 13A:
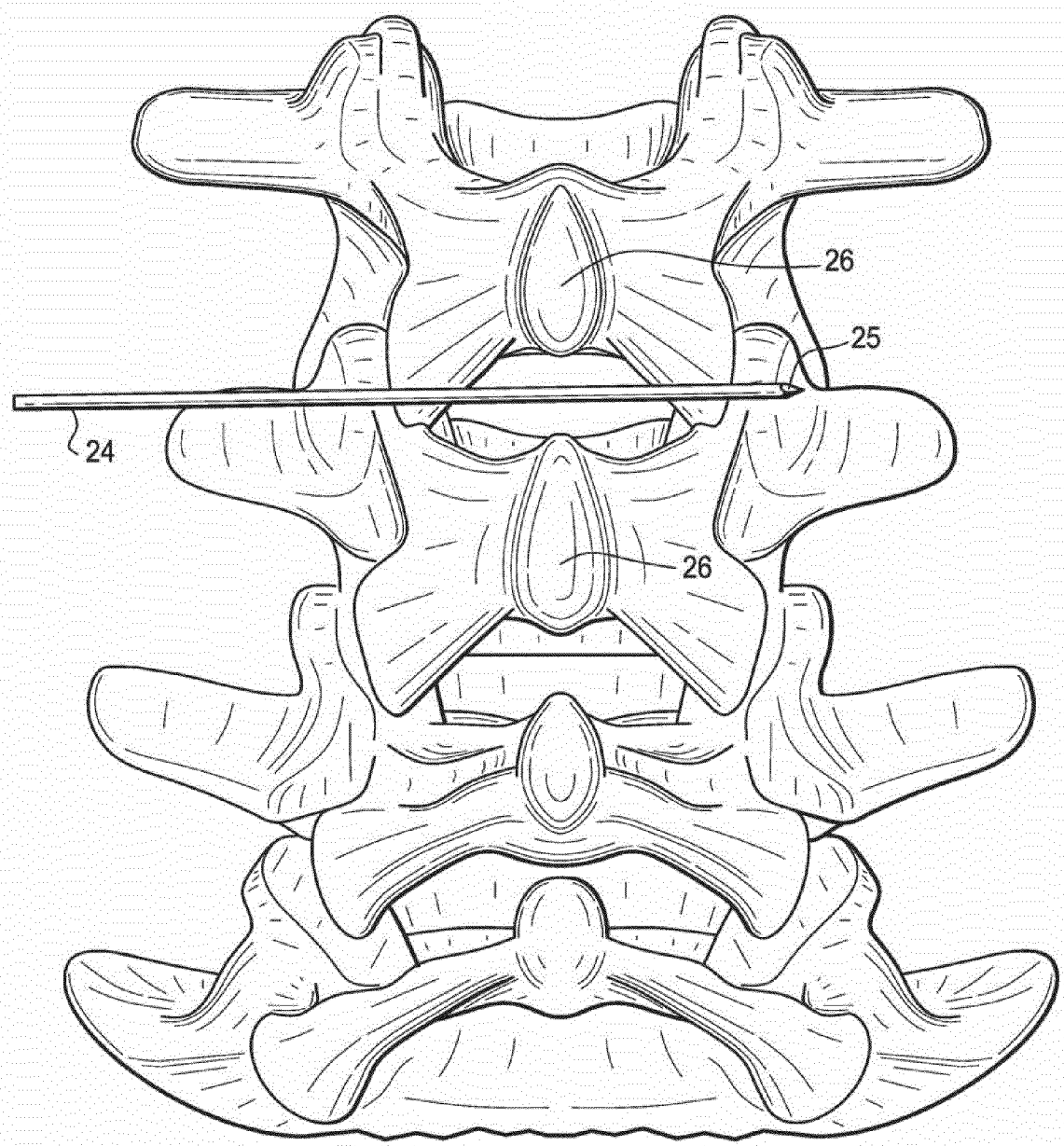

FIGS. 13A-13H illustrate a method of performing interspinous distraction according to an exemplary embodiment of the present invention. The method includes inserting a guide wire 24 having a pointed tip 25 between the two spinous processes 26 (FIG. 13A). The guide wire 24 is configured to guide the insertion of the distractor 12 and the inserting of the insertion driver 20 between the two spinous processes 26 while the insertion driver 20 is coupled to the distractor 12. The distractor 12 and the insertion driver 20 each have a guide channel 19 disposed therein configured to accept the guide wire 24 therein.

Figure 13B:
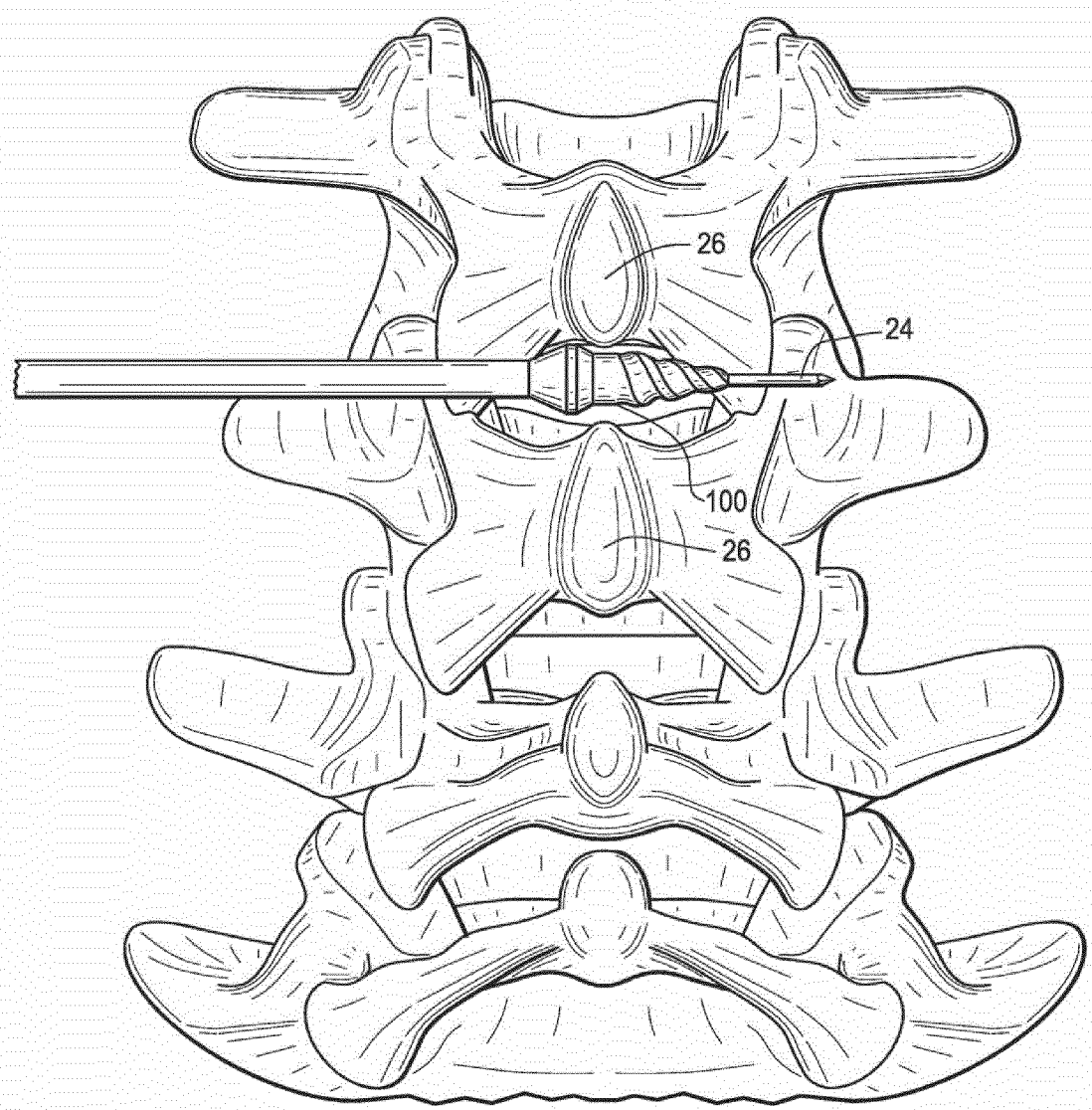

Provisional dilation of the spinous processes 26 is performed with cannulated conical screw or smooth semi conical shape dilators 100 and 100, as shown in FIGS. 13B and 13C. During provisional dilation, the first dilator 100 is inserted via the guide wire 24 and cuts through the interspinous ligament (not shown) using the sharp edges 117A, 118A. The dilator 100 distracts the spinous processes 26 if the dilator 100 comes into contact with the spinous processes 26. Then, the first dilator 100 is removed.

If the first dilator 100 does not contact the spinous processes 26, a second dilator 101 is inserted via the guide wire 24. The second dilator 101 is larger than the first dilator 100 and also cuts through the interspinous ligament. If necessary, several dilators 100, 101, etc. can be used until one of the dilators contacts the spinous processes 26. The dilators can have slightly increasing outer diameters. For example, a 6 mm, an 8 mm, a 10 mm, a 12 mm, and a 14 mm dilator can be used.

Contact between the dilator and the spinous processes 26 can be felt due to the tension provided between the spinous processes 26 by the super spinous ligament (not shown).

Once the proper size is determined by the dilator, a distractor of an appropriate size can be selected.

Figure 13D:
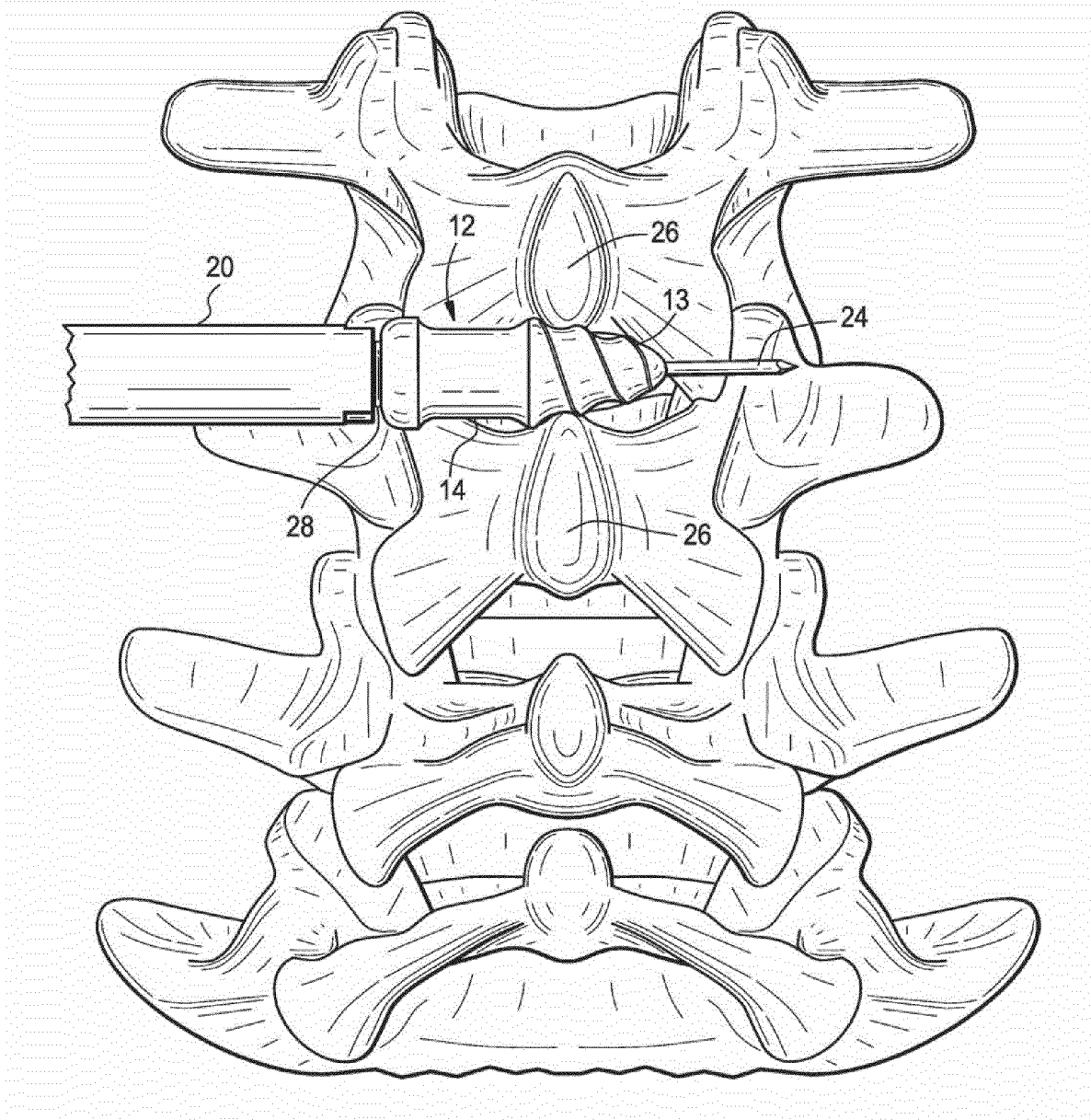

The method further includes inserting the distractor 12 having a conical insertion portion 13 and a central engagement groove 14 between the two spinous processes 26 (FIG. 13D). The conical insertion portion 13 is adapted such that a gradual distraction between the two spinous processes occurs 26. The insertion drive 20 acts as a device holding tool for inserting the distractor 12 between the spinous processes 26. Thus, FIG. 13D also illustrates inserting the insertion driver 20 while coupled to the distractor 12, the insertion driver 20 being detachably coupled to a rear portion 28 of the distractor 12.

Figure 13E:
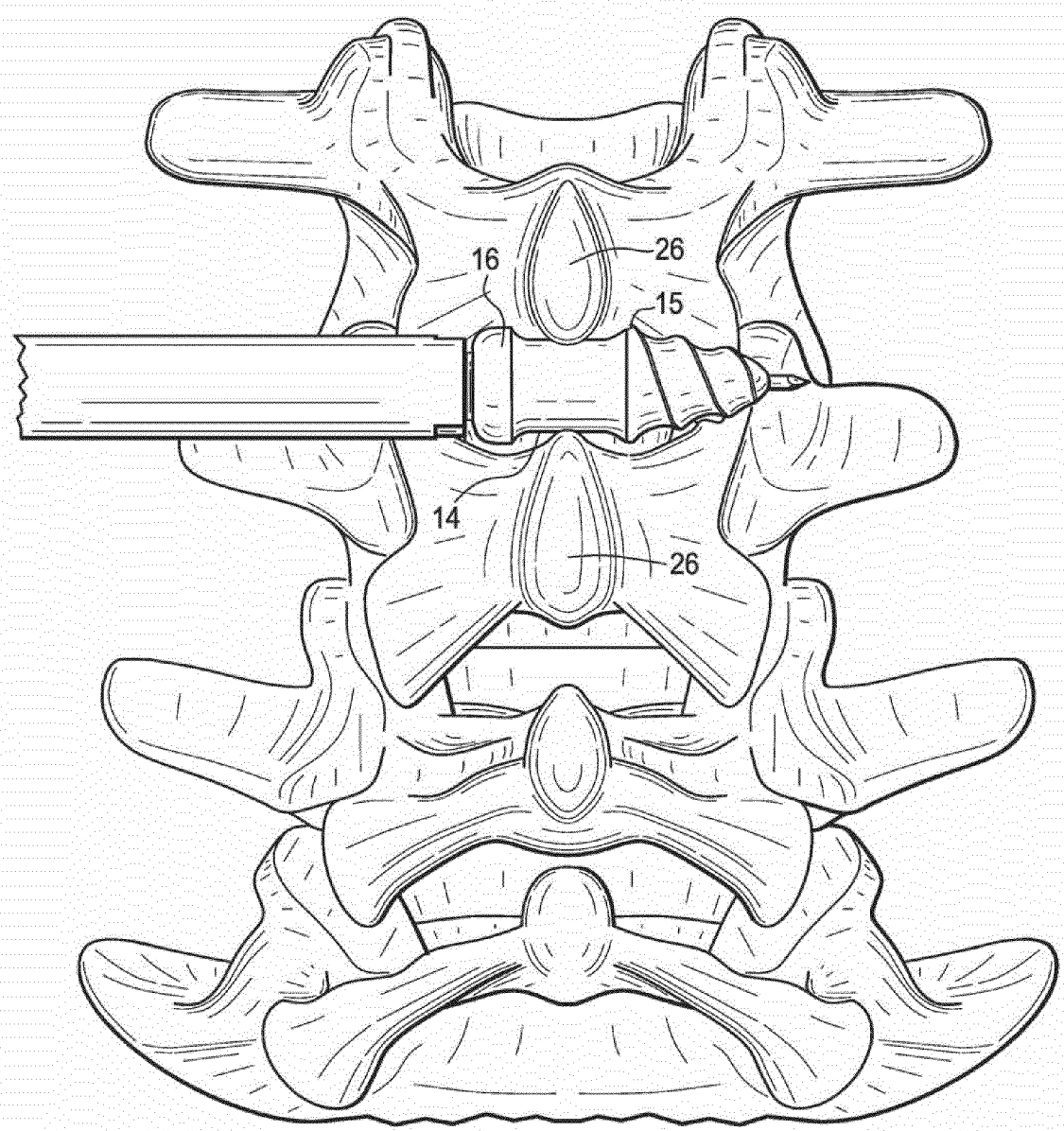

The method further includes implanting the distractor 12 between the two spinous processes 26 such that the two spinous processes 26 rest in the central engagement groove 14 between a proximal end 15 and a distal end 16 of the central engagement groove 14 (FIG. 13E).

Figure 13F:
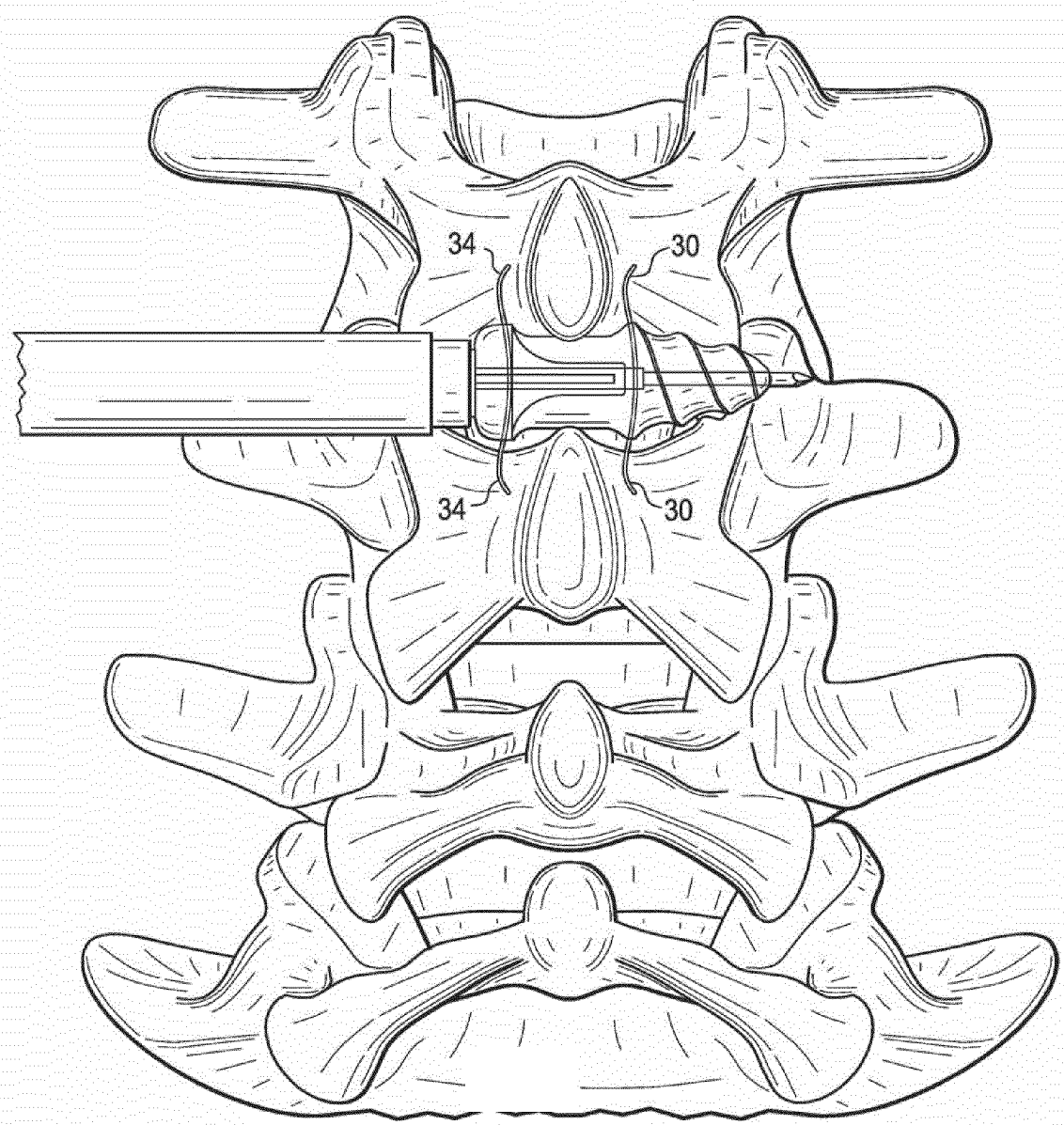
Figure 13G:
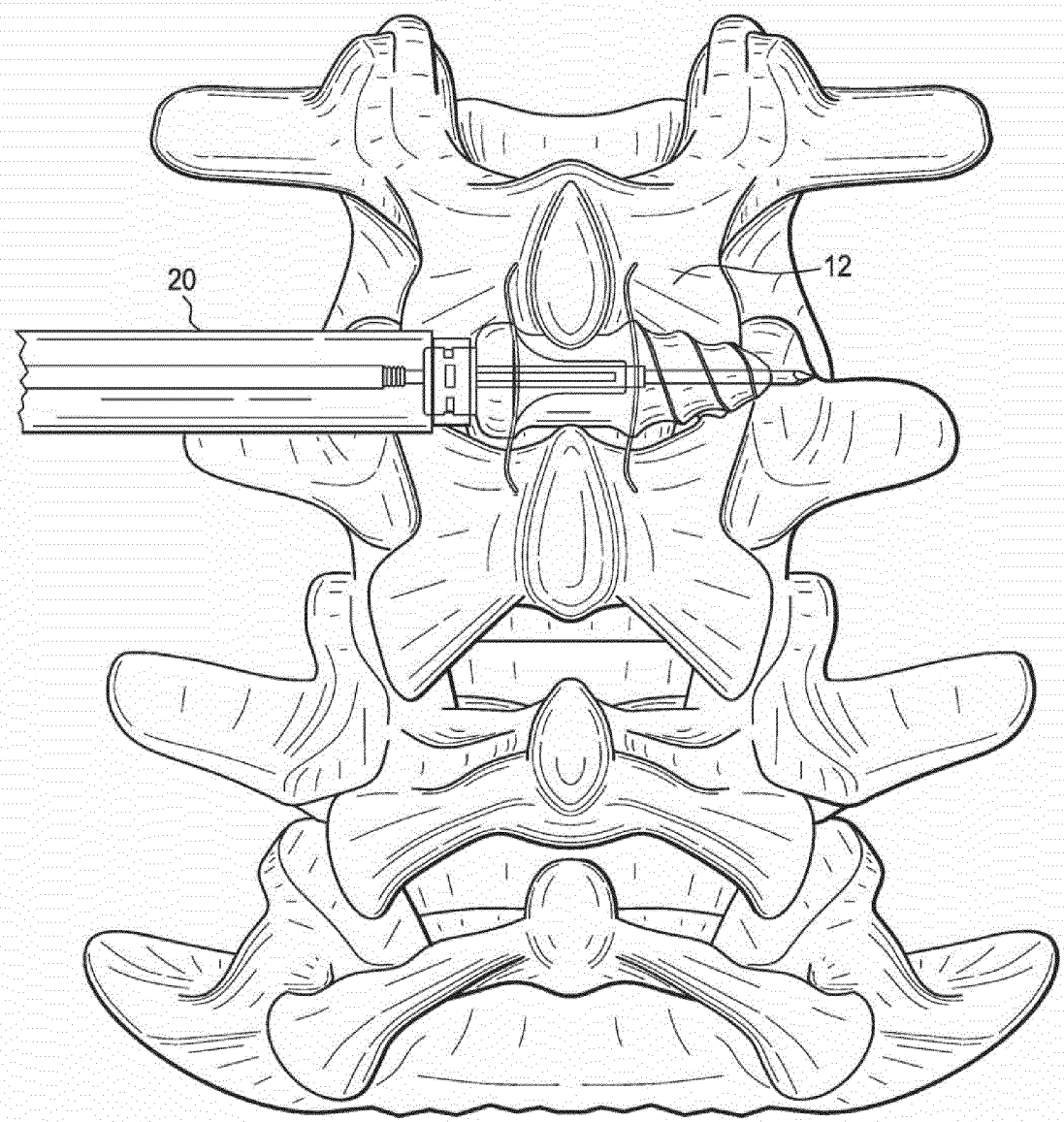
Figure 13H:
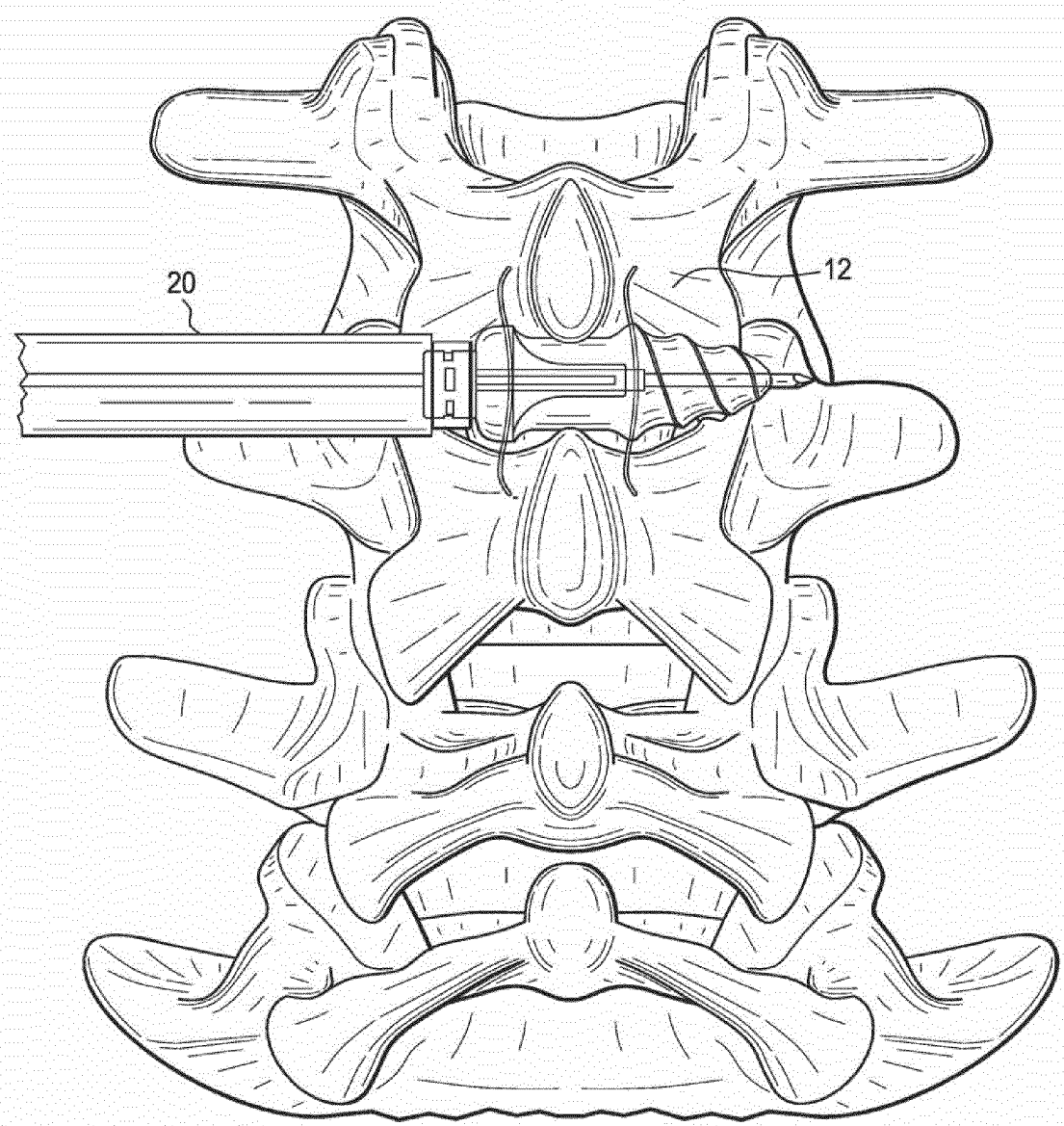

The method further includes deploying a stabilizer (e.g., stabilization wings 30 and 34) which is adapted to be deployed from within the distractor 12 to secure the two spinous processes 26 within the central engagement groove 14 (FIG. 13F). The stabilizer may also be locked into the deployed state (FIG. 13F).

Figure 13I:
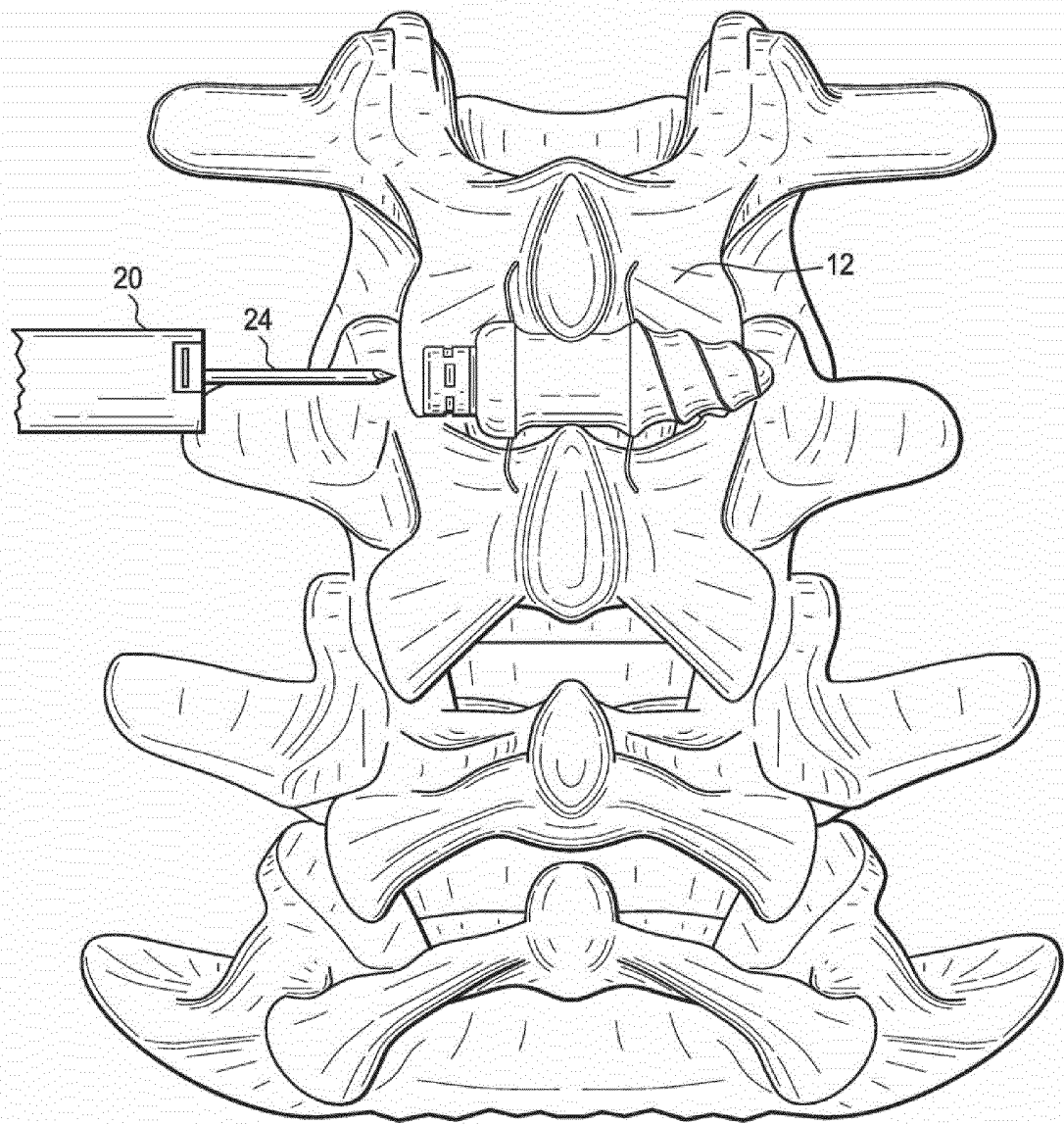

The method further includes decoupling the insertion driver 20 from the distractor 12 (FIGS. 13G and 13H) and removing the insertion driver 20 and the guide wire 24 (FIG. 13I).

FIGS. 14A-14H illustrate an interspinous apparatus according to another exemplary embodiment of the present invention. In this embodiment, the apparatus can be clamped onto the spinous process after being implanted.

Figure 14A:
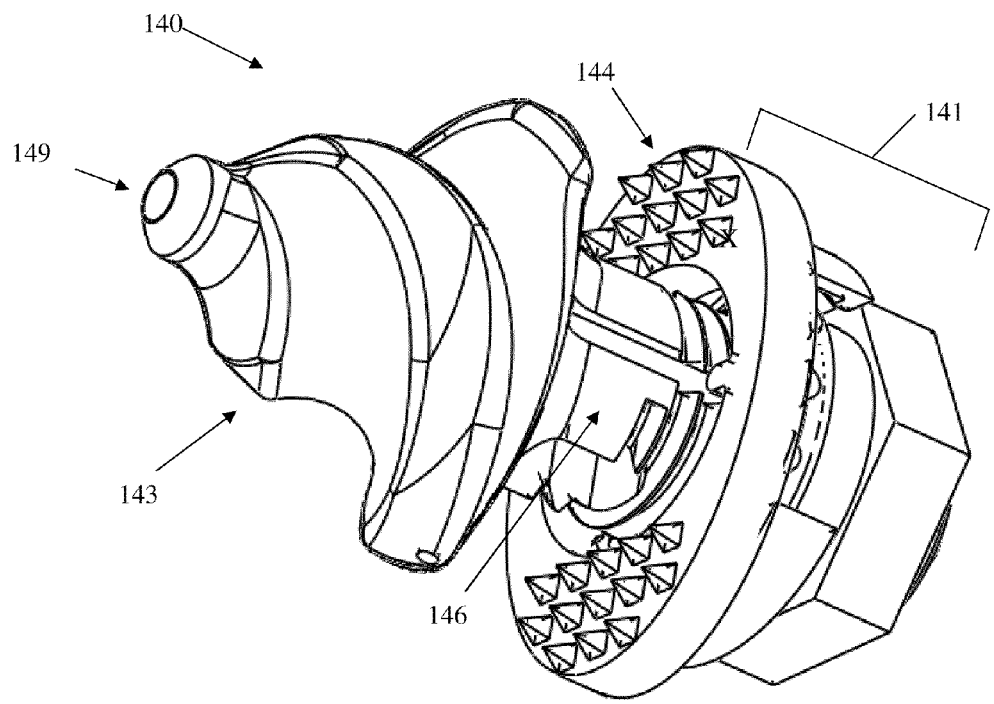
FIGS. 14A-14H illustrate an interspinous apparatus according to another exemplary embodiment of the present invention.

FIG. 14A shows the features of the apparatus including the insertion portion 143 and guide channel 149, as explained above, as well as a shaft 146, which is connected to the insertion portion 143 and passes through the clamp 141. In this particular embodiment, clamp 141 is shown in an elliptical shape, however, the clamp 141 could also be circular, rectangular, or any other advantageous shape. Teeth 144 may be present on the clamp 141 and are configured to create additional friction between the bony mater of the spinous process and the clamp 141. The teeth 144 can be sharp and shaped accordingly having a conical, pyramidal or other desired shape.

Figure 14B:
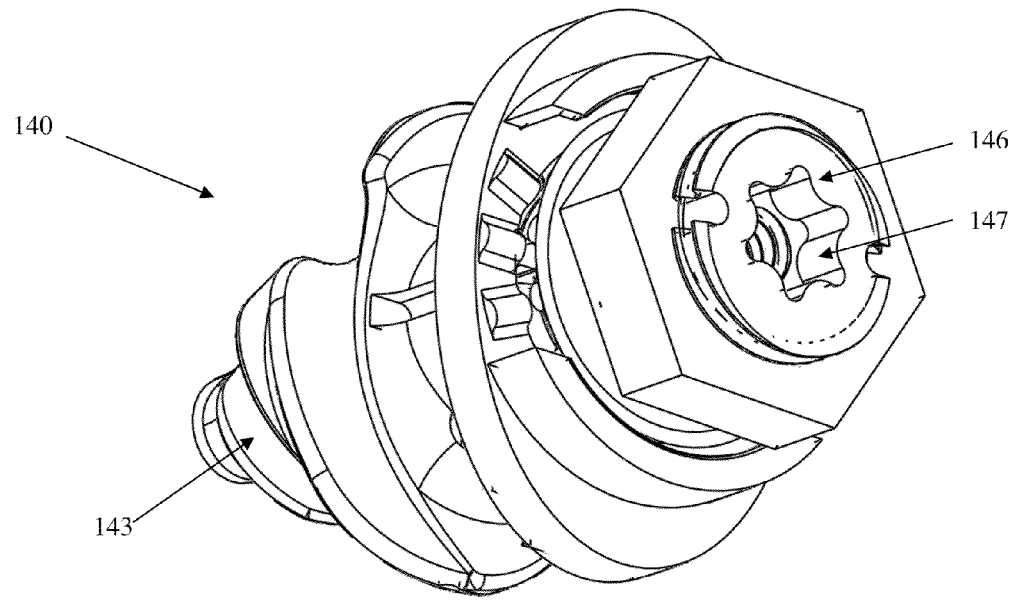

FIG. 14B better illustrates the distal end of the apparatus including the distal end of the shaft 146, and instrument mating feature 147, where an insertion driver 20 (shown in FIG. 3) or any other instrument can be attached for the purpose of implantation, removal, repositioning, etc. of the implant.

Figure 14C:
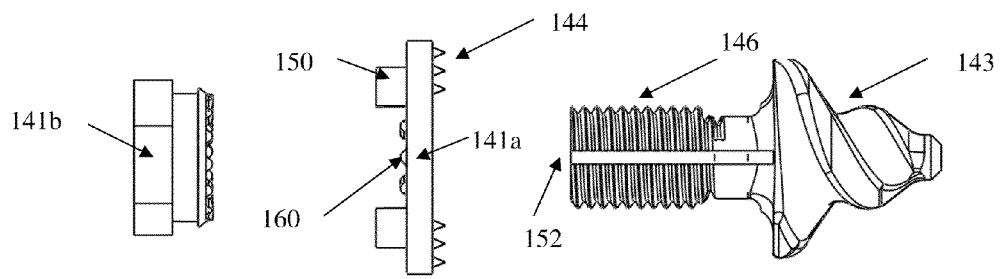
Figure 14D:
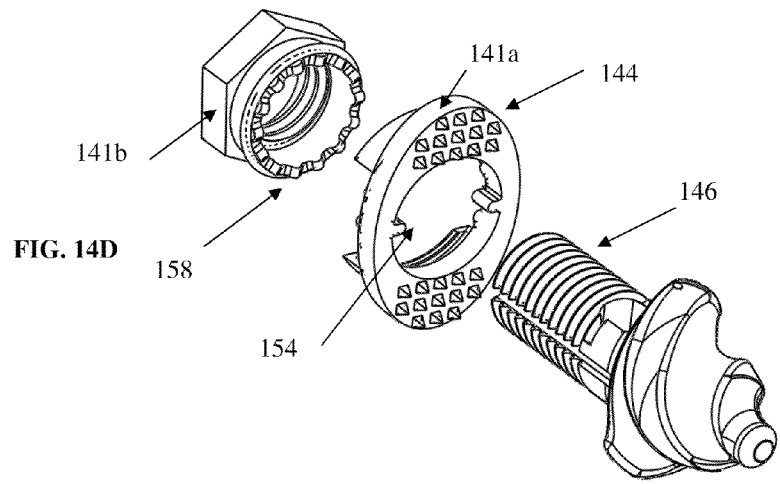
Figure 14E:
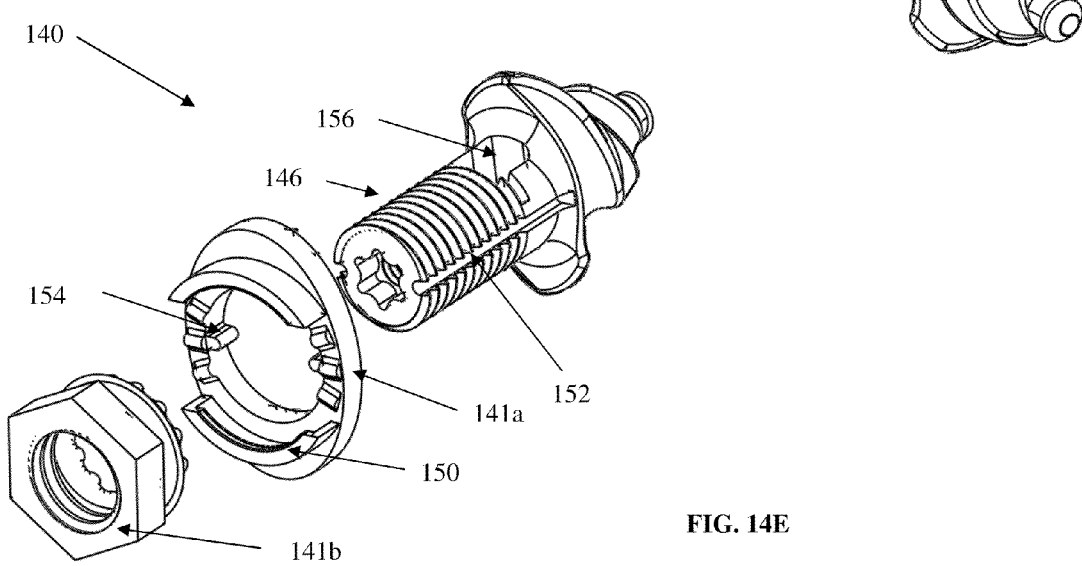

FIGS. 14C-14E specifically show one particular embodiment of the apparatus 140 where the clamp 141 has two parts: a washer 141a and a retention nut 141b. In these figures, the apparatus is shown disassembled into its three main parts: washer 141a, retention nut portion 141b, and insertion portion 143. As shown in FIG. 14C, the shaft 146 can have a cross-section that is smaller than that of the distal end of the insertion portion 143. The smaller cross-section of the shaft portion is configured to secure the distractor between the two spinous processes such that the two spinous processes rest on the shaft portion. The shaft 146 may be threaded, as shown, stepped, have a frictioned surface or smooth.

After the apparatus 140 has been inserted between the spinous processes, it can be clamped to the spinous processes by advancing the retention nut 141b, which in this embodiment is in a rotational manner, toward the washer 141a and the insertion portion 143. The spinous process becomes clamped between the distal end of the insertion portion 143 and the washer 141a. When adequate compression has been achieved the retention nut 141b automatically locks to the washer 141a when features 160 and 158 mate and prevent rotation of the washer 141a and nut 141b. To further secure the clamp 141a and the retention nut 141b together, the retention nut 141b can be surrounded by one or more retention lips 150, located on the washer 141a, configured to have a rim to grasp onto a mating rim of the retention nut 141b.

Washer protrusions 160 and the retention nut protrusions 158 are meant to mate together to prevent rotation after final tightening of the retention nut 141b with respect to the shaft 146. This is necessary to prevent the retention nut 141b from unscrewing and allowing the assembly to come apart after implantation. Protrusions 158 and 160 can be any shape including semi-cylindrical, as shown. The apparatus 140 may contain a full circle of protrusions 158 and 160 around the washer 141a and retention nut 141b openings, or the protrusions 158 and 160 strategically placed on only certain portions of the washer 141a and retention nut 141b.

Alternate embodiments can contain at least one orientation slot 152 which interlocks with at least one orientation key 154 to keep the shaft 146, and washer 141a properly aligned. In other embodiments there may be a graft cavity 156, which is configured to retain biological material, such as a bone graft, to promote bone fusion.

Figure 14F:
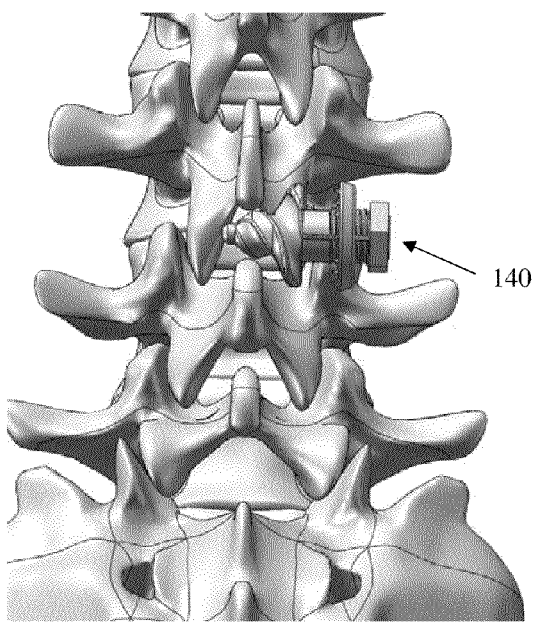
Figure 14G:
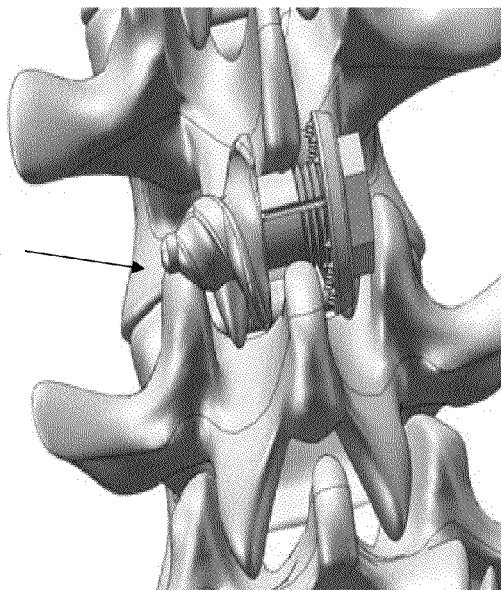
Figure 14H:
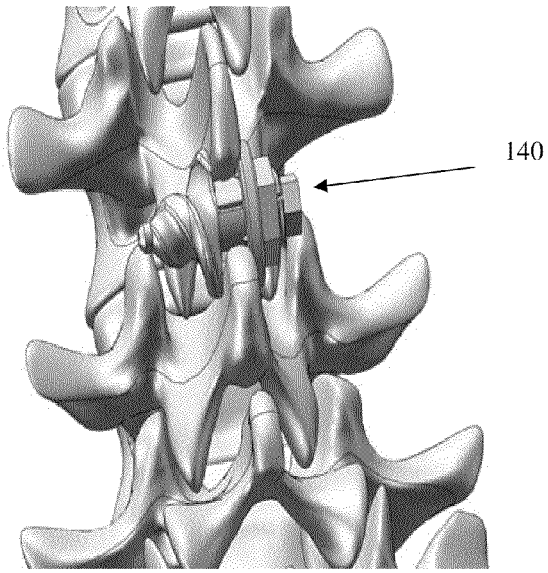

FIGS. 14F-14H illustrate the apparatus 140 as it is inserted between two spinous processes. Initially, as shown in FIG. 14F, the apparatus 140 is in its "open" position where the washer 141a and retention nut 141b are farther from the insertion portion 143 than when the apparatus 140 is in its "clamped" position as show in FIG. 14H. FIG. 14G shows the apparatus 140 in its final position before the retention nut 141b is tightened and the clamp 141a is secured to the spinous process.

What is claimed is:

1. A method of performing interspinous distraction, the method comprising:
    inserting a guide wire having a pointed tip between the two spinous processes;
    inserting a distractor having a conical insertion portion and a shaft between two spinous processes of vertebrae, the conical insertion portion configured such that a gradual distraction between the two spinous processes occurs;
    inserting an insertion driver while coupled to the distractor, the insertion driver being detachably coupled to a rear portion of the distractor, wherein the guide wire is configured to guide the inserting of the distractor and the inserting of the insertion driver between the two spinous processes while the insertion driver is coupled to the distractor, wherein the distractor and the insertion driver each have a guide channel disposed therein configured to accept the guide wire therein;
    implanting the distractor between the two spinous processes such that the two spinous processes rest on the shaft between a proximal end and a distal end of the shaft;
    advancing a clamp along the shaft until it abuts the spinous process;
    tightening the clamp; and
    decoupling the insertion driver from the distractor and removing the insertion driver.

2. The method of claim 1, wherein the inserting of the distractor includes screwing the distractor into place between the two spinous processes, wherein the insertion portion has a conical screw shape such that a surface of the insertion portion has screw-shaped grooves configured to enable the distractor to be screwed into place between the two spinous processes during the inserting of the distractor.

3. The method of claim 1, wherein the insertion portion has an axis of distraction having a constant increasing angle that provides for constant distraction during the inserting of the distractor.

4. The method of claim 1 wherein the clamp includes a retention nut portion and a washer portion.

5. A conical interspinous apparatus comprising:
   a distracter comprising:
      an insertion portion with a proximal end, a distal end, and conical screw-shaped grooves configured to distract two adjacent spinous processes;
      a shaft portion, coupled to the distal end of the insertion portion, and having a smaller cross-section than a cross-section at the distal end of the insertion portion, such that the two spinous processes rest on the shaft portion;
   a clamp portion being movable and securable along the shaft portion, and being configured to secure the two spinous processes between the clamp portion and the distal end of the insertion portion;
   an insertion driver detachably coupled to the distractor;
   a guide wire having a pointed tip, the guide wire being adapted for insertion between the two spinous processes, the guide wire configured to guide the inserting of the distractor and the inserting of the insertion driver between the two spinous processes while the insertion driver is coupled to the distractor; and
   wherein the distractor and the insertion driver each have a guide channel disposed therein configured to accept the guide wire therein.

6. The conical interspinous apparatus of claim 5, wherein the clamp portion includes a retention nut portion and a washer portion.

7. The conical interspinous apparatus of claim 6, wherein at least one of the washer portion and the retention nut portion further comprises at least one protrusion configured to mate together to prevent rotation of the clamp after implantation.

8. The conical interspinous apparatus of claim 6, wherein the washer is elliptical in shape.

9. The conical interspinous apparatus of claim 6, wherein the washer portion further comprises retention lips configured to secure the retention nut portion to the washer portion.

10. The conical interspinous apparatus of claim 5, wherein the clamp portion is elliptical in shape.

11. The conical interspinous apparatus of claim 5, wherein the insertion portion has an axis of distraction having a constant increasing angle that provides for constant distraction.

12. The conical interspinous apparatus of claim 5, wherein the insertion portion further comprises an ungrooved tip.

13. The conical interspinous apparatus of claim 5, wherein the clamp has teeth configured to create additional friction between the bony mater of the spinous process and the clamp.

14. The conical interspinous apparatus of claim 5, wherein the shaft is threaded.

15. The conical interspinous apparatus of claim 5, wherein the shaft portion comprises a graft cavity configured to retain graft material within the apparatus.

16. The conical interspinous apparatus of claim 5, wherein the shaft portion further comprises at least one orientation slot, which mates with at least one orientation key located on the washer portion, the slot configured to keep the shaft portion and washer portion properly aligned.

* * * * *